United States Patent [19]

Christensen et al.

[11] 4,424,230

[45] Jan. 3, 1984

[54] 6-(1'-HYDROXYETHYL)-3-SUBSTITUTED AMINO-1-AZABICYCLO-[3.2.0]HEPT-2-EN-7-ONE-2-CARBOXYLIC ACID

[75] Inventors: Burton G. Christensen, Scotch Plains; Ronald W. Ratcliffe, Matawan, both of N.J.

[73] Assignee: Merck & Co., Inc., Rahway, N.J.

[21] Appl. No.: 167,592

[22] Filed: Jul. 11, 1980

Related U.S. Application Data

[63] Continuation-in-part of Ser. No. 843,613, Oct. 19, 1977, abandoned.

[51] Int. Cl.³ .................. C07D 487/04; C07D 205/08; A61K 31/40; A61K 31/495
[52] U.S. Cl. ............................. 424/274; 260/245.2 T; 424/200; 424/248.5; 424/248.53; 424/248.55; 424/250; 424/267; 544/80; 544/121; 544/130; 544/357; 544/364; 544/373; 546/187; 546/200; 546/272
[58] Field of Search ................ 260/245.2 T; 424/274, 424/200, 248. 5, 248.55, 248.53, 250, 267; 544/357, 364, 373, 80, 121, 130; 546/187, 200, 272

[56] References Cited

U.S. PATENT DOCUMENTS 4,217,453 8/1980 Christensen et al. ........ 260/245.2 T

OTHER PUBLICATIONS

Morrison et al.: Organic Chemistry, p. 727 (1969).
Thielheimer; Synthetic Methods, vol. 11:496 (1956).

*Primary Examiner*—Mark L. Berch
*Attorney, Agent, or Firm*—Daniel T. Szura; Hesna J. Pfeiffer; James A. Arno

[57] ABSTRACT

Disclosed are 6-(1'-hydroxyethyl)-3-substituted amino-1-azabicyclo[3.2.0]hept-2-en-7-one-2-carboxylic acids (I):

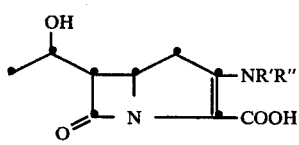

wherein R' and R" are independently selected from H, substituted and unsubstituted alkyl and aralkyl groups, or together form a substituted or unsubstituted cyclic group. Such compounds and their O- and carboxyl derivatives are useful as antibiotics. Also disclosed are processes for the preparation of such compounds, pharmaceutical compositions comprising such compounds and methods of treatment comprising administering such compounds and compositions when an antibiotic effect is indicated.

4 Claims, No Drawings

6-(1'-HYDROXYETHYL)-3-SUBSTITUTED AMINO-1-AZABICYCLO-[3.2.0]HEPT-2-EN-7-ONE-2-CARBOXYLIC ACID

BACKGROUND OF THE INVENTION

This application is a continuation-in-part of U.S. patent application Ser. No. 843,613 filed Oct. 19, 1977 now abandoned.

This invention relates to 6-(1'-hydroxyethyl)-3-substituted amino-1-azabicyclo[3.2.0]hept-2-en-7-one-2-carboxylic acids and their pharmaceutically acceptable salt, ester and amide derivatives (I) which are useful as antibiotics:

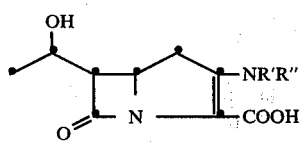

wherein R' and R" are independently selected from hydrogen; substituted or unsubstituted: alkyl and cycloalkyl having from 1-10 carbon atoms, aralkyl such as phenylalkyl and heterocyclylalkyl wherein the alkyl has 1-6 carbon atoms and the hetero atom or atoms are selected from O, N and S, and cyclic groups wherein R' and R" are joined; and wherein the ring or chain substituent or substituents on R', R" or the cyclic radical formed by their joinder are selected from the group consisting of amino, mono-, di- and trialkylamino (each alkyl having from 1-6 carbon atoms), hydroxyl, carboxyl, alkoxyl having from 1-6 carbon atoms, halo, such as chloro, bromo and fluoro nitro, —$SO_2NH_2$, phenyl, benzyl, and alkoxylcarbonyl having 1-3 carbon atoms in the alkoxyl moiety.

This invention also relates to the O- and/or carboxyl derivatives of I which are antibiotics and which may be represented by the following generic structure (I):

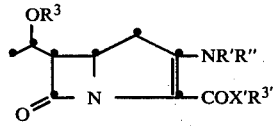

wherein X' is oxygen, sulphur or NR° (R°=H or lower alkyl having 1-6 carbon atoms); and $R^{3'}$ is, inter alia, representatively selected from the group consisting of hydrogen, conventional blocking groups such as trialkylsilyl, acyl and the pharmaceutically acceptable salt, ester and amide moieties known in the bicyclic β-lactam antibiotic art; the definition of $R^{3'}$ is given in greater detail below; $R^3$ is, in addition to hydrogen, (1.) acyl (generically the group $OR^3$ is classifiable as an ester); or (2.) $R^3$ is selected from alkyl, aryl, aralkyl and the like (such that the group $OR^3$ is generically classifiable as an ether). The term "acyl" is by definition inclusive of the alkanoyls including derivatives and analogues thereof such as thio analogues wherein the carbonyl oxygen is replaced by sulphur; as well as sulphur and phosphorous acyl analgoues such as substituted sulfonyl-, sulfinyl-, and sulfenyl- radicals, and substituted P (III and V) radicals such as substituted phosphorous-, phosphoric-, phosphonous- and phosphonic- radicals, respectively. Such acyl radicals of the present invention are further defined below, as are the radicals (2., above) which constitute the ether embodiments of the present invention.

This invention also relates to processes for the preparation of such compounds (I); pharmaceutical compositions comprising such compounds; and to methods of treatment comprising administering such compounds and compositions when an antibiotic effect is indicated.

There is a continuing need for new antibiotics. For unfortunately, there is no static effectiveness of any given antibiotic because continued wide scale usage selectively gives rise to resistant strains of pathogens. In addition, the known antibiotics suffer from the disadvantage of being effective only against certain types of microorganisms. Accordingly the search for new antibiotic continues.

Thus, it is an object of the present invention to provide a novel class of antibiotics which are useful in animal and human therapy and in inanimate systems. These antibiotics are active against a broad range of pathogens which representatively include both gram positive bacteria such as *S. aureus, Strep. pyogenes, B. subtilis* and gram negative bacteria such as *E. coli, Proteus morganii,* Pseudomonas, Serratia and Klebsiella. Further objects of this invention are to provide chemical processes for the preparation of such antibiotics and their non-toxic pharmaceutically acceptable salts; pharmaceutical compositions comprising such antibiotics; and to provide methods of treatment comprising administering such antibiotics and compositions when an antibiotic effect is indicated.

DETAILED DESCRIPTION OF THE INVENTION

The compounds of the present invention are conveniently prepared by the following scheme:

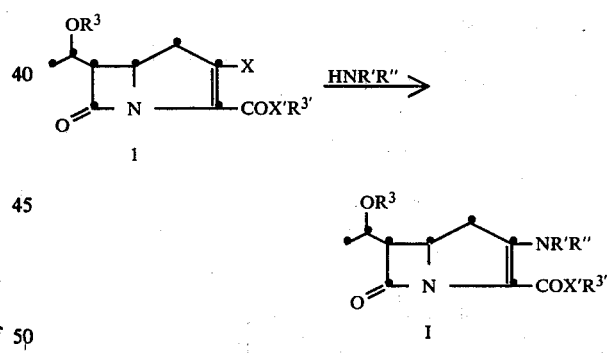

In words, relative to the above reaction diagram, the compounds of the present invention may be prepared from common starting material 1. This starting material is disclosed and claimed in co-pending, commonly assigned U.S. patent application Ser. No. 160,717 (filed June 18, 1980) now U.S. Pat. No. 4,318,912 of Christensen and Ratcliffe, which application is incorporated herein by reference. The 3-substituent in the starting material is a leaving group X preferably selected from chloro, bromo, —OMs (methanesulfonyloxy), or —OTs (p-toluenesulfonyloxy). The radicals $R^3$, X' and $R^{3'}$ of the starting material 1 are as defined above for the compounds of the present invention (structure I, above).

The compounds of the present invention may be prepared, as shown in the above diagram, by treating starting material 1, wherein X is the above-described leaving group, with a primary or secondary amine HNR'R". The reaction is conducted in a solvent such as ethanol (EtOH) dioxane, dimethylformamide (DMF), hexamethylphosphoramide (HMPA) or the like at a temperature of from 0° to 50° C. for from 1 to 24 hours.

Relative to the generic representation of the compounds of the present invention, preferred representative values for the 3-substituent —NR'R" are:
—NH$_2$,
—NHCH$_2$CH$_3$,
—NH(CH$_2$)$_2$CH$_3$,
—NHCH(CH$_3$)$_2$,
—NHCH(CH$_3$)CH$_2$CH$_3$,
—NHCH$_2$CH(CH$_3$)$_2$,
—NH(CH$_2$)$_2$CH(CH$_3$)$_2$,
—NH(CH$_2$)$_2$C(CH$_3$)$_3$,
—NHCH(CH$_3$)(CH$_2$)$_4$CH$_3$,
—NHCH(CH$_3$)CH(CH$_3$)$_2$,
(CH$_2$)$_n$CH—NH—
(CH$_2$)$_n$CH—CH$_2$NH—(n=2-6)

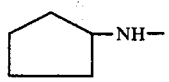

—NHCH$_2$CH$_2$OH,
—NHCH(CH$_2$CH$_3$)CH$_2$OH,
—NH(CH$_2$)$_4$CH$_2$OH,
—NHCH(CH$_3$)CH$_2$OH,
—NHCH$_2$C(CH$_3$)$_2$OH,
—NH(CH$_2$)$_2$CH$_2$OH,
—NH(CH$_2$)$_3$CO$_2$CH$_2$CH$_3$,
—NH(CH)CH$_3$CH$_2$CO$_2$CH$_2$CH$_3$,
—NHCH$_2$CH$_2$OCH$_3$,
—NHCH$_2$CF$_3$,
—NHCH$_2$CH$_2$N(CH$_3$)$_2$,
—NH(CH$_2$)$_3$N(CH$_3$)$_2$,
—NHCH(CH$_3$)(CH$_2$)$_3$N(C$_2$H$_5$)$_2$,

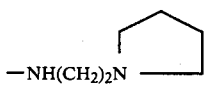

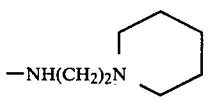

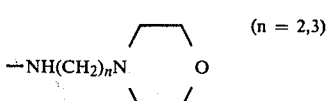

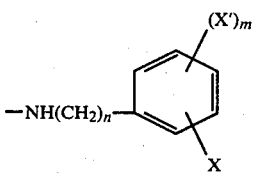

(n=1-3; m=1 or 0; X=H, CH$_3$, OCH$_3$, Cl, Br, F, NO$_2$, OH, SO$_2$NH$_2$),

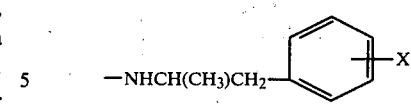

(X=OH, CH$_3$),
—NHCH$_2$CH($\phi$)$_2$ ($\phi$=phenyl),
—NHCH$_2$CH($\phi$)CH$_2$OH
—NHCH$_2$CH$_2$CH($\phi$),

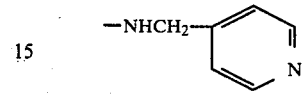

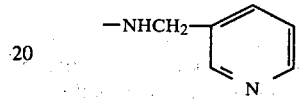

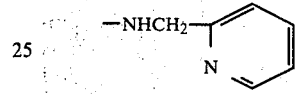

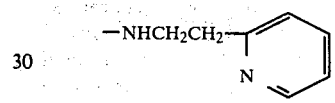

—NHCH$_3$,
—N(C$_2$H$_5$)$_2$,
—N(CH$_2$CH$_2$CH$_3$)$_2$,
—N(CH$_2$CH$_2$CH$_2$CH$_3$)$_2$,
—N(CH$_3$)(CH$_2$CH$_3$),
N(CH$_2$CH$_3$)CH$_2$CH$_2$N(C$_2$H$_5$)$_2$,
—N(CH$_3$)(CH$_2$CH$_2$CH$_2$CH$_3$),

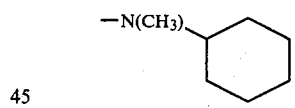

—N(CH$_2$CH$_2$OCH$_2$CH$_3$)$_2$,
—N(CH$_2$CH$_2$CH$_2$CH$_3$)CH$_2$CH$_2$OH,
—N(CH$_3$)CH$_2$CH$_2$N(CH$_3$)$_2$,
—N(CH$_2$CH$_3$)(CH$_2$CH$_2$CH$_2$CH$_3$),
—N(CH$_2$CH$_3$)(CH$_2$CH$_2$OH),
—N(CH$_2$CH$_2$OH)$_2$,
—N(CH$_3$)CH$_2\phi$
—N(CH$_2\phi$)CH$_2$CH$_2$N(CH$_3$)$_2$,
—N(CH$_2\phi$)CH$_2$CH$_2$OH,
—N(CH$_3$)CH$_2$CH(OH)$\phi$,
—N(CH$_2$CH$_3$)CH$_2\phi$,

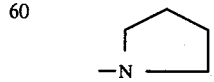

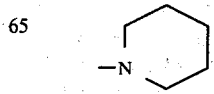

-continued

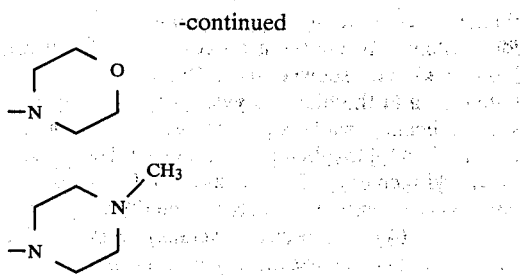

As mentioned above, the compounds of the present invention may be prepared as pharmaceutically acceptable O— and carboxyl derivatives. Of course, it is understood that the value of $R^3$ in the above reaction diagram may be hydrogen and the X' may be oxygen and that $R^{3'}$ may be any readily removable blocking group such as benzyl, p-nitrobenzyl, o-nitrobenzyl and the like. Removal of such blocking groups is conveniently effected by hydrolysis or hydrogenation. Thus, when the carboxyl blocking group benzyl is employed, the most convenient deblocking procedure is hydrogenation at 1-4 atmospheres $H_2$ at 25° C. in a solvent such as EtOH, EtOAc, dioxane, $H_2O$, or the like in the presence of a catalyst such as Pd, Pd/C, or $PtO_2$.

Alternatively, the radicals $R^3$, $X'$ and $R^{3'}$ may be established after the above reaction scheme, if desired, and may have the identities disclosed in the above-cited, and incorporated by reference U.S. patent application Ser. No. 160,717 filed June 18, 1980 now U.S. Pat. No. 4,318,912.

IDENTIFICATION OF THE RADICAL —COX'R³'

In the generic representation of the compounds of the present invention (I, above), the radical represented by —COX'R³' is, inter alia, —COOH (X' is oxygen and R³' is hydrogen) and all radicals known to be effective as pharmaceutically acceptable ester, anhydride (R³' is acyl) and amide radicals in the bicyclic β-lactam antibiotic art, such as the cephalosporins and penicillins and the nuclear analogues thereof.

Suitable radicals ($R^{3'}$) include conventional protecting or carboxyl blocking groups. The term "blocking group" as utilized herein is employed in the same manner and in accordance with the teaching of U.S. Pat. No. 3,697,515 which is incorporated herein by reference. Pharmaceutically acceptable derivatives of the present invention falling in this class are given below. Suitable blocking esters thus include those selected from the following list which is representative and not intended to be an exhaustive list of possible ester groups, wherein X'=O and R³' is given:

(i) $R^{3'}=CR^aR^bR^c$ wherein at least one of $R^a$, $R^b$ and $R^c$ is an electron-donor, e.g., p-methoxyphenyl, 2,4,6-trimethylphenyl, 9-anthryl, methoxy, $CH_2SCH_3$, tetrahydrofur-2-yl, tetrahydropyran-2-yl or fur-2-yl. The remaining $R^a$, $R^b$ and $R^c$ groups may be hydrogen or organic substituting groups. Suitable ester groups of this type include p-methoxybenzyloxycarbonyl and 2,4,6-trimethylbenzyloxycarbonyl.

(ii) $R^{3'}=CR^aR^bR^c$ wherein at least one of $R^a$, $R^b$ and $R^c$ is an electron-attracting group, e.g, benzoyl, p-nitrophenyl, 4-pyridyl, trichloromethyl, tribromomethyl, iodomethyl, cyanomethyl, ethoxycarbonylmethyl, arylsulphonylmethyl, 2-dimethylsulphoniummethyl, o-nitrophenyl or cyano. Suitable esters of this type include benzoylmethoxycarbonyl p-nitrobenzyloxycarbonyl, 4-pyridylmethoxycarbonyl, 2,2,2-trichloroethoxycarbonyl and 2,2,2-tribromoethoxycarbonyl.

(iii) $R^{3'}=CR^aR^bR^c$ wherein at least two of $R^a$, $R^b$ and $R^c$ are hydrocarbon such as alkyl, e.g., methyl or ethyl, or aryl, e.g., phenyl and the remaining $R^a$, $R^b$ and $R^c$ group, if there is one, is hydrogen. Suitable esters of this type include t-butyloxycarbonyl, t-amyloxycarbonyl, diphenylmethoxycarbonyl and triphenylmethoxycarbonyl.

(iv) $R^{3'}=R^d$, wherein $R^d$ is adamantyl, 2-benzyloxyphenyl, 4-methylthiophenyl or tetrahydropyran-2-yl.

Silyl esters, under this category of blocking groups, may conveniently be prepared from a halosilane or a silazane of the formula: $R^4{}_3SiX'$; $R^4{}_2SiX'{}_2$; $R^4{}_3SiNR^4{}_2$; $R^4{}_3Si.NH.COR^4$; $R^4{}_3Si.NH.CO.NH.SiR^4{}_3$; $R^4NH.CO.NH^4.SiR^4{}_3$; or $R^4C(OSiR^4{}_3)$; $HN(SiR^4{}_3)_2$ wherein X' is a halogen such as chloro or bromo and the various groups $R^4$, which can be the same or different, represent hydrogen atoms or alkyl, e.g., methyl, ethyl, n-propyl, isopropyl; aryl, e.g., phenyl; or aralkyl, e.g., benzyl groups.

More generally stated, pharmaceutically acceptable carboxyl derivatives of the present invention are those derived by reacting I with alcohols, phenols, mercaptans, thiophenols, acylating reagents and the like. For example, esters and amides of interest are the above-listed starting materials and final products having the following group at the 2-position of the thienamycin nucleus: —COX'R³' wherein X' is oxygen, sulfur, or NR' (R' is H or R³'), and R³' is alkyl having 1-10 carbon atoms, straight or branched, such as methyl, ethyl, t-butyl, pentyl, decyl and the like; carbonylmethyl, including phenacyl, p-bromophenacyl, p-t-butylphenacyl, acetoxyacetylmethyl, pivaloxyacetylmethyl, carboxymethyl, and its alkyl and aryl esters, α-carboxy-α-isopropyl; aminoalkyl including 2-methylaminoethyl, 2-diethylaminoethyl, 2-acetamidoethyl, phthalimidomethyl, succinimidomethyl; alkoxyalkyl wherein the alkoxy portion has 1-10 and preferably 1-6 carbon atoms; but can be branched, straight or cyclic, and the alkyl portion has 1-6 carbon atoms, such as methoxymethyl, ethoxymethyl, isopropoxymethyl, decyloxymethyl, ethoxypropyl, decyloxypentyl, cyclohexyloxymethyl and the like; alkanoyloxyalkyl wherein the alkanoyloxy portion is straight or branched and has 1-6 carbon atoms and the alkyl portion has 16 carbon atoms, such as acetoxymethyl, pivaloyloxymethyl, acetoxyethyl, propionyloxyethyl, acetoxypropyl, and the like; haloalkyl wherein halo is chloro, bromo, fluoro, or iodo, and the alkyl portion is straight or branched having 1-6 carbon atoms, e.e., 2,2,2-trichloroethyl, trifluoroethyl, 2-bromopropyl, diiodomethyl, 2-chloroethyl, 2-bromoethyl, and the like; alkenyl having 1-10 carbon atoms, either straight or branched, e.g., allyl, 2-propenyl, 3-butenyl, 4-butenyl, 4-pentenyl, 2-butenyl, 3-pentenyl, 3-methyl-3-butenyl, metallyl, 1,4-cyclohexadien-1-yl-methyl, and the like alkynyl having 1-10 carbon atoms, either straight or branched e.g., 3-pentenyl, propargyl, ethynyl, 3-butyn-1-yl, and the like; alkanoyl, either straight or branched, having 1-10 carbon atoms, such as pivaloyl, acetyl, propionyl, and the like; aralkyl or heteroaralkyl wherein alkyl has 1-3 carbon atoms, and hetero means 1-4 hetero atoms being selected from the group consisting of O, S, or N, such as benzyl, benzhydryl, and substituted benzyl, benzhydryl, or e.g., benzyl or benzhydryl substituted with 1-3 substituents such as benzyl, phenoxy, halo, loweralkyl, loweralkanoyloxy of 1-5 carbon atoms, lower alkoxy, hydroxy, nitro, blocked carboxy, or combinations thereof, e.g., p-chlorobenzyl, o-nitrobenzyl, 3,5-dinitrobenzyl, p-methoxybenzyl, m-benzoylbenzyl, p-t-butylbenzyl, m-phenoxybenzyl, p-benzoylbenzyl, p-nitrobenzyl, 3,5-dichloro-4-hydroxybenzyl, p-methoxycarbonylbenzyl, p-methoxybenzhydryl, p-carboxybenzyl, the latter being either the free acid, ester or the sodium salt, 2,4,6-trimethylbenzyl, p-pivaloyloxybenzyl, p-t-butoxycarbonyl benzyl, p-methylbenzyl, p-benzoyloxybenzyl, p-acetoxybenzyl, p-2-ethylhexanoylbenzyl, p-ethoxycarbonylbenzyl, p-benzoylthiobenzyl, p-benzamidobenzyl, o-pivaloyloxybenzyl, m-pivaloyloxybenzyl, p-isopropoxybenzyl, p-t-butoxybenzyl, as well as the cyclic analogues thereof, 2,2-dimethyl-5-coumaranmethyl, 5-indanylmethyl, p-trimethylsilylbenzyl, 3,5-bis-t-butoxy-4-hydroxybenzyl; 2-thienylmethyl, 2-furylmethyl, 3-t-butyl-5-isothiazolmethyl, 6-pivaloyloxy-3-pyridazinylethyl, 5-phenylthio-1-tetrazolylmethyl, or the like (the use of the terms lower alkyl or lower alkoxy in this context means 1-4 carbon atoms chain); or phthalidyl; or phenylethyl, 2-(p-methylphenyl)ethyl, and the arylthioalkyl analogues, aryloxyalkyl wherein aryl is preferably a phenyl ring having 0-3 substituents preferably 0 or 1 substituents in the ortho or para positions and alkyl is 1-6 carbon atoms, e.g., (4-methoxy)phenoxymethyl, phenoxymethyl, (4-chloro)phenoxymethyl, (4-nitro)phenoxymethyl, (4-benzyloxy)phenoxymethyl, (4-methyl)phenoxymethyl, (4-benzyloxy)phenoxymethyl, (4-methyl)phenoxymethyl, (2-methoxy)phenoxymethyl, (1-phenoxy)ethyl, (4-amino)phenoxymethyl, (4-methoxy)phenylthiomethyl, (4-chloro)phenylthiomethyl, phenylthioethyl; aryl wherein aryl is phenyl, 5-indanyl, or substituted phenyl having 0-3 substituents, preferably 0 or 1 substituent in the ortho or para position, e.g., (4-methyl)phenyl, (4-hydroxy)phenyl, (4-t-butyl)phenyl, p-nitrophenyl, 3,5-dinitrophenyl, or p-carboxyphenyl, the latter having either the free acid or the sodium salt form; aralkenyl wherein aryl is phenyl and alkenyl has 1-6 carbon atoms, such as 3-phenyl-2-propenyl; aralkoxyalkyl wherein aralkoxy is benzyloxy, and alkyl has 1-3 carbon atoms, such as benzyloxymethyl, (4-nitro)-benzyloxymethyl, (4-chloro)benzyloxymethyl; alkylthioalkyl wherein the alkylthio portion has 1-10 and preferably 1-6 carbon atoms, but can be branched, straight or cyclic, and the alkyl portion has 1-6 carbon atoms, such as methylthioethyl, ethylthioethyl, cyclohexylthiomethyl, decylthiobutyl, methylthiopropyl, isopropylthioethyl, methylthiobutyl and the like.

In addition to the esters (and thio esters) listed above, amides are also embraced by the present invention, i.e., wherein X' is the

group. Representative of such amides are those wherein R' is selected from the group consisting of hydrogen, methyl, ethyl, phenyl, p-methoxyphenyl, benzyl, carboxymethyl, methylthioethyl, and heteroaryl; also embraced by —COX'R³' are anhydrides wherein R³' is acyl, for example, benzyloxycarbonyl, ethoxycarbonyl, benzoyl, and pivaloyl.

The most preferred —COX'R³' radicals of the present invention are those wherein (relative to Structure I above) X' is oxygen, sulphur or NR' (R' is selected from the group consisting of hydrogen and lower alkyl); and R³' is selected from the group consisting of: loweralkyl, lower alkenyl, such as methallyl, 3-methylbutenyl, 3-butenyl, and the like; methylthioethyl; benzyl and substituted benzyl such as p-t-butylbenzyl, m-phenoxybenzyl, p-pivaloyloxybenzyl, p-nitrobenzyl and the like; pivaloyloxymethyl, 3-phthalidyl and acetoxymethyl, propionyloxymethyl, acetylthiomethyl, pivaloylthiomethyl, allyl, 4-butenyl, 2-butenyl, 3-methyl-2-butenyl, phenacyl, acetoxyacetylmethyl, methoxymethyl, p-acetoxybenzyl, p-pivaloyloxybenzyl, p-isopropoxybenzyl, 5-indanylmethyl, 5-indanyl, benzyloxymethyl, ethylthioethyl, methylthiopropyl, methoxycarbonyloxymethyl, ethoxycarbonyloxymethyl, dimethylaminoacetoxymethyl, crotonolacton-3-yl, and acetamidomethyl.

IDENTIFICATION OF R³

In the generic representation of the present invention, Structure I (above), the radical R³ is, in addition to hydrogen, (1.)acyl (generically the group —OR³ is classifiable as an ester); or (2.) R³ is selected from alkyl, aryl, aralkyl, and the like such that the group —OR³ is classifiable as an ether. For the ester embodiments (1) R³ is selected from the following definition of acyl radicals (p=1). In the so-called ether embodiments (2.) of the present invention, R³ is selected from the same acyl radicals wherein the carbonyl moiety,

or more generally

is deleted (p=0); thus R³ is selected from the following radicals wherein all symbolism is defined below:

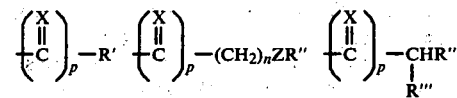

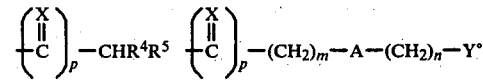

Thus, relative to the definition of R³, the acyl radical can, inter alia, be substituted or unsubstituted aliphatic, aromatic or heterocyclic, araliphatic or heterocyclylaliphatic carboxylic acid radical, a substituted or unsubstituted carbamyl radical or a carbothioic acid radical. One group of acyl radicals can be represented by the general formula:

wherein X is O or S and R" represents hydrogen; amino; substituted amino such as alkyl- and dialkylamino wherein the alkyl radical comprises 1 to about 6 carbon atoms; substituted or unsubstituted: straight or branched chain alkyl wherein the alkyl radical comprises 1 to about 6 carbon atoms; mercapto, aryloxy, typically comprising 6 to 10 carbon atoms; alkenyl, or alkynyl groups typically comprising 2 to 6 carbon atoms; aryl such as phenyl; aralkyl such as benzyl; cycloalkyl, typically comprising 3 to 6 carbon atoms; or a heteroaryl or heteroaralkyl group (mono- and bicyclic) wherein the alkyl moiety typically comprises 1 to 3 carbon atoms and the heterocyclic ring comprises typically 4 to 10 atoms and the hetero atom or atoms are selected from O, N and S; such above-listed groups can be unsubstituted or can be substituted by radicals such as OH, SH, SR (R is lower alkyl or aryl such as phenyl, alkyl or alkoxy groups having 1 to about 6 carbon atoms, halo, such as Cl, Br, R and I, cyano, carboxy, sulfamino, carbamoyl, sulfonyl, azido, amino, substituted amino such as alkylamino including quaternary ammonium wherein the alkyl group comprises 1 to 6 carbon atoms, haloalkyl such as trifluoromethyl, carboxyalkyl, carbamoylalkyl, N-substituted carbamoylalkyl, wherein the alkyl moiety of the foregoing four radicals comprises 1 to about 6 carbon atoms, amidino, guanidino, N-substituted guanidino, guanidino lower alkyl and the like. Representative examples of such acyl groups that might be mentioned are those wherein R'' is benzyl, p-hydroxybenzyl, 4-amino-4-carboxybutyl, methyl, cyanomethyl, 2-pentenyl, n-amyl, n-heptyl, ethyl 3- or 4-nitrobenzyl, phenethyl, β,β-diphenylethyl, methyldiphenylmethyl, triphenylmethyl, 2-methoxyphenyl, 2,6-dimethoxyphenyl, 2,4,6-trimethoxyphenyl, 3,5-dimethyl-4-isoxazolyl, 3-butyl-5-methyl-4-isoxazolyl, 5-methyl-3-phenyl-4-isoxazolyl, 3-(2-chlorophenyl)-5-methyl-4-isoxazolyl, 3-(2,6-dichlorophenyl)5-methyl-4-isoxazolyl, D-4-amino-4-carboxybutyl, D-4N-benzoylamino-4-carboxy-n-butyl, p-aminobenzyl, o-aminobenzyl, m-aminobenzyl, p-dimethylaminobenzyl, (3-pyridyl)methyl, 2-ethoxy-1-napthyl, 3-carboxy-2-quinoxalinyl, 3-(2,6-dichlorophenyl)-5-(2-furyl)-4-isoxazolyl, 3-phenyl-4-isoxazolyl, 5-methyl-3-(4-guanidinophenyl)4-isoxazolyl, 4-guanidinomethylphenyl, 4-guanidinomethylbenzyl, 4-guanidinobenzyl, 4-guanidinophenyl, 2,6-dimethoxy-4-guanidino, o-sulfobenzyl, p-carboxymethylbenzyl, p-carbamoylmethylbenzyl, m-fluorobenzyl, m-bromobenzyl, p-chlorobenzyl, p-methoxybenzyl, 1-naphthylmethyl, 3-isothiazolylmethyl, 4-isothiazolylmethyl, 5-isothiazolylmethyl, guanylthiomethyl, 4-pyridylmethyl, 5-isoxazolylmethyl, 4-methoxy-5-isoxazolylmethyl, 4-methyl-5-isoxazolylmethyl, 1-imidazolylmethyl, 2-benzofuranylmethyl, 2-indolylmethyl, 2-phenylvinyl, 2-phenylethynyl, 1-aminocyclohexyl, 2- and 3-thienylaminomethyl, 2-(5-nitrofuranyl)vinyl, phenyl, o-methoxyphenyl, o-chlorophenyl, o-phenylphenyl, p-aminomethylbenzyl, 1-(5-cyanotriazolyl)methyl, difluoromethyl, dichloromethyl, dibromomethyl, 1-(3-methylimidazolyl)methyl, 2- or 3-(5-carboxymethylthienyl)methyl, 2- or 3-(4-carbamoylthienyl)methyl, 2- or 3-(5-methylthienyl)methyl, 2- or 3-(methoxythienyl)methyl, 2- or 3-(4-chlorothienyl)methyl, 2- or 3-(5-sulfothienyl)methyl, 2- or 3-(5-carboxythienyl)methyl, 3-(1,2,5-thiadiazolyl)methyl, 3-(4-methxoy-1,2,5-thiadiazolyl)methyl, 2-furylmethyl, 2-(5-nitrofuryl)-methyl, 3-furylmethyl, 2-thienylmethyl, 3-thienylmethyl, tetrazolylmethyl, benzamidinomethyl and cyclohexylamidinomethyl.

The acyl group can also be a radical of the formula:

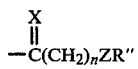

wherein X is O or S and n is 0-4, Z represents oxygen, sulfur, carbonyl or nitrogen and R'' is defined as above. Representative members of the substituent

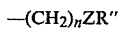

that might be mentioned are allylthiomethyl, phenylthiomethyl, butylmercaptomethyl, α-chlorocrotylmercaptomethyl, phenoxymethyl, phenoxyethyl, phenoxybutyl, phenoxybenzyl, diphenoxymethyl, dimethylmethoxyethyl, dimethylbutoxymethyl, dimethylphenoxymethyl, 4-guanidinophenoxymethyl, 4-pyridylthiomethyl, p-(carboxymethyl)phenoxymethyl, p-(carboxymethylphenylthiomethyl, 2-thiazolylthiomethyl, p-(sulfo)phenoxymethyl, p-(carboxymethyl)phenylthiomethyl, 2-pyrimidinylthiomethyl, phenethylthiomethyl, 1-(5,6,7,8-tetrahydronaphthyl)oxomethyl, N-methyl-4-pyridylthio, benzyloxy, methoxy, ethoxy, phenoxy, phenylthio, amino, methylamino, dimethylamino, pyridinium methyl, trimethylammoniummethyl, cyanomethylthiomethyl, trifluoromethylthiomethyl, 4-pyridylethyl, 4-pyridylpropyl, 4-pyridylbutyl, 3-imidazolylethyl, 3-imidazolylpropyl, 3-imidazolylbutyl, 1-pyrroloethyl, 1-pyrrolopropyl, and 1-pyrrolobutyl.

Alternatively, the acyl group can be a radical of the formula:

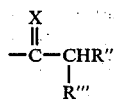

wherein R'' is defined as above and R''' is a radical such as amino, hydroxy, azido, carbamoyl, guanidino, amidino, acyloxy, halo, such as Cl, F, Br, I, sulfamino, tetrazolyl, sulfo, carboxy, carbalkoxy, phosphono and the like. Representative members of the substituent

that might be mentioned are α-aminobenzyl, α-amino-(2-thienyl)methyl, α-(methylamino)benzyl, α-aminomethylmercaptopropyl, α-amino-3- or 4-chlorobenzyl, α-amino-3- or 4-hydroxybenzyl, α-amino-2,4-dichlorobenzyl, α-amino-3,4-dichlorobenzyl, D(—)-α-hydroxybenzyl, α-carboxybenzyl, α-amino-(3-thienyl)methyl D(—)-α-amino-3-chloro-4-hydroxybenzyl, α-amino(cyclohexyl)methyl, α-(5-tetrazolyl)benzyl, 2-thienyl-carboxymethyl, 3-thienyl-carboxymethyl, 2-furylcarboxymethyl, 3-furyl-carboxymethyl, α-sulfaminobenzyl, 3-thienyl-sulfaminomethyl, α-(N-methylsulfamino)-benzyl D(—)-2-thienyl-guanidinomethyl, D(—)-α-guanidinobenzyl α-guanylureidobenzyl, α-hydroxybenzyl, α-azidobenzyl, α-fluorobenzyl, 4-(5-methoxy-1,3-oxadiazolyl)-aminomethyl, 4-(5-methoxy-1,3-oxadiazolyl)-hydroxymethyl, 4-(5-methoxy-1,3-sulfadiazolyl)-hydroxymethyl, 4-(5-chlorothienyl)aminomethyl, 2-(5-chlorothienyl)-hydroxymethyl, 2-(5-chlorothienyl)-carboxy-methyl, 3-(1,2-thiazolyl)-aminomethyl, 3-(1,2-thiazolyl)-hydroxymethyl, 3-(1,2- thiazolyl)carboxymethyl, 2-(1,4-thiazolyl)-aminomethyl, 2-(1,4-thiazolyl)-hydroxymethyl, 2-(1,4-thiazolyl)carboxymethyl, 2-benzothienylaminomethyl, 2-benzothienylhydroxymethyl, 2-benzothienylcarboxymethyl, α-sulfobenzyl, α-phosphonobenzyl, α-diethylphosphono, and α-monoethylphosphono. Further acyl radicals of interest in this class when X=oxygen are:

wherein $R^4$ and $R^5$ are as defined below. $R^4$ represents hydrogen, halo, such as chloro, fluoro, bromo, iodo, amino, quanidino, phosphono, hydroxy, tetrazolyl, carboxy, sulfo, or sulfamino and $R^5$ represents phenyl, substituted phenyl, a mono- or bicyclic heterocyclyl containing one or more oxygen, sulfur or nitrogen atoms in the ring, such as furyl, quinoxalyl, thienyl, quinolyl, quinazolyl, thiazolyl, siothiazolyl, tetrazolyl, oxadiazolyl, thiadiazolyl and and the like substituted heterocycles, phenylthio, phenyloxy lower alkyl of 1–6 carbon atoms, heterocyclic or substituted heterocyclic thio groups; or cyano. The substituents on the moieties, $R^4$ and $R^5$, can be halo, carboxymethyl, guanidino, guanidinomethyl, carboxamidomethyl, aminomethyl, nitro, methoxy or methyl. When $R^4$ is selected from the group consisting of hydrogen, hydroxy, amino or carboxy and $R^5$ is selected from the group consisting of phenyl, or a 5- or 6-membered heterocyclic ring having one or two sulfur, oxygen or nitrogen hetero atom such as tetrazolyl, thienyl, furyl and phenyl, the following acyl radicals are representative: phenylacetyl 3-bromophenylacetyl, p-aminomethylphenylacetyl, 4-carboxymethylphenylacetyl, 4-carboxyamidomethylphenylacetyl, 2-furylacetyl, 5-nitro-2-furylacetyl, 3-furylacetyl, 2-thienylacetyl, 5-chloro-2-thienylacetyl, 5-methoxy-2-thienylacetyl, α-guanidino-2-thienylacetyl, 3-thienylacetyl, 2-(4-methylthienyl)acetyl, 3-isothiazolylacetyl, 4-methoxy-3-isothiazolylacetyl, 4-isothiazolylacetyl, 3-methyl-4-isothiazolylacetyl, 5-isothiazolylacetyl, 3-chloro-5-isothiazolylacetyl, 3-methyl-1,2,5-oxadiazolylacetyl, 1,2,5-thiadiazolyl-4-acetyl, 3-methyl-1,2,5-thiadiazolylacetyl, 3-chloro-1,2,5-thiadiazolylacetyl, 3-methoxy-1,2,5-thiadiazolylacetyl, phenylthioacetyl, 4-pyridylthioacetyl, cyanoacetyl, 1-tetrazolylacetyl, α-fluorophenylacetyl, D-phenylglycyl, 4-hydroxy-D-phenylglycyl, 2-thienylglycyl, 3-theinylglycyl, phenylmalonyl, 3-chlorophenylmalonyl, 2-thienylmalonyl, 3-thienylmalonyl, α-phosphonophenylacetyl, α-amino cyclohexadienylacetyl, α-sulfaminophenylacetyl, α-hydroxyphenylacetyl, α-tetrazolylphenylacetyl and α-sulfophenylacetyl.

The acyl radical may be selected from sulphur (1) and phosphorous (2) radicals:

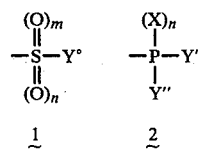

wherein with respect to 1, m and n are integers selected from 0 or 1 and $Y°=O^\ominus M^\oplus$, $-N(R'')_2$, and $R''$; wherein $M^\oplus$ is selected from hydrogen, alkali metal cations and organic bases; and $R''$ is as defined above, e.g., alkyl, alkenyl, aryl and heteroaryl. With respect to 2 X=O or S; n=0 or 1; and Y' and Y'' are selected from the group consisting of $O^\ominus M^\oplus$, $-N(R'')_2$, $R''$ and $ZR''$ wherein all symbolism is as defined above, e.g., $R''$ and $ZR''$ are representatively: alkyl, alkenyl, aryl, heteroaryloxy, Y' and Y'', including $R''$ moieties, can be joined together to form cyclic ester, ester- amide and amide functions.

An acyl class of particular interest is those acyl radicals which are selected from the group consisting of conventionally known N-acyl blocking or protective groups such as carbobenzyloxy, ring-sbustituted carbobenzyloxy such as o- and p-nitrocarbobenzyloxy, p-methoxycarbobenzyloxy, chloroacetyl, bromoacetyl, phenylacetyl, t-butoxycarbonyl, trifluoroacetyl, bromoethoxycarbonyl, 9-fluorenylmethoxycarbonyl, dichloroacetyl, o-nitrophenylsulfenyl, 2,2,2-trichloroethoxycarbonyl, bromo-t-butoxycarbonyl, phenoxyacetyl; non-acyl protective groups such as trilower alkyl silyl, for example, trimethylsilyl and t-butyldimethyl are also of interest.

The following radicals, according to the foregoing definition of acyl, are especially preferred for $R^3$ of structure Ia: formyl, acetyl, propionyl, butyryl, chloroacetyl, methoxyacetyl, aminoacetyl, methoxycarbonyl, ethoxycarbonyl, methylcarbamoyl, ethylcarbamoyl, phenylthiocarbonyl, 3-aminopropionyl, 4-aminobutyryl, N-methylaminoacetyl, N,N-dimethylaminoacetyl, N,N,N-trimethylaminoacetyl, 3-(N,N-dimethyl)aminopropionyl, 3-(N,N,N-trimethyl)aminopropionyl, N,N,N-triethylaminoacetyl, pyridiniumacetyl, guanidinoacetyl, 3-guanidinopropionyl, $N^3$-methylguanidinopionyl, hydroxyacetyl, 3-hydroxypropionyl, acryloyl, propynoyl, malonyl, phenoxycarbonyl, amidinoacetyl, acetamidinoacetyl, amidinopropionyl, acetamidinopropionyl, guanylureidoacetyl, guanylcarbamoyl, carboxymethylaminoacetyl, sulfoacetylaminoacetyl, phosphonoacetylaminoacetyl, $N^3$-dimethylaminoacetamidinopropionyl, ureidocarbonyl, dimethylaminoguanylthioacetyl, 3-(1-methyl-4-pyridinium)propionyl, 3-(5-aminoimidazol-1-yl)propionyl, 3-methyl-1-imidazoliumacetyl, 3-sydnonylacetyl, o-aminomethylbenzoyl, o-aminobenzoyl, sulfo, phosphono,

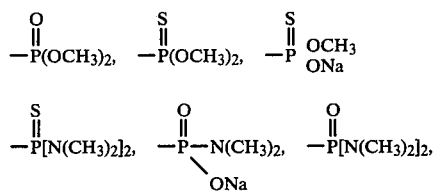

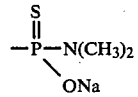

Another class of acyl radicals are terminally substituted acyls wherein the substituent is a basic group such as substituted and unsubstituted: amino, amidino, guanidino, guanyl and nitrogen-containing mono- and bicyclic heterocycles (aromatic and non-aromatic) wherein the hetero atom or atoms, in addition to nitrogen, are selected from oxygen and sulphur. Such substituted acyls may be represented by the following formula:

wherein m, and n are integers selected from 0 to 5; A is O, NR' (R' is hydrogen or loweralkyl having 1-6 carbon atoms), S or A represents a single bond; and Y° is selected from the following group:

(1) amino or substituted amino

—N(R°)$_2$ and —N$^+$(R°)$_3$ wherein the values for R° are independently selected from: hydrogen; N(R')$_2$ (R' is hydrogen or loweralkyl having 1-6 carbon atoms); loweralkyl and loweralkoxyl having from 1 to 6 carbon atoms; loweralkoxyloweralkyl wherein the alkoxyl moiety comprises 1 to 6 carbon atoms and the alkyl moiety comprises 2-6 carbon atoms; cycloalkyl and cycloalkylalkyl wherein the cycloalkyl moiety comprises 3-6 carbon atoms and the alkyl moiety comprises 1-3 carbon atoms, two R° groups may be joined together with the N atom to which they are attached to form a ring having 3-6 atoms.

(2) amidino and substituted amidino

wherein the value of R° is independently selected from the group consisting of: hydrogen; N(R')$_2$ (R' is hydrogen or loweralkyl having 1-6 carbon atoms); loweralkyl and loweralkoxyl having from 1 to 6 carbon atoms, loweralkoxyloweralkyl wherein the alkoxyl moiety comprises 1 to 6 carbon atoms and the alkyl moiety comprises 2 to 6 carbon atoms (when the loweralkoxyloweralkyl radical is attached to carbon the alkyl moiety comprises 1 to 6 carbon atoms); cycloalkyl and cycloalkylalkyl wherein the alkyl moiety comprises 1 to 3 carbon atoms; two R groups may be joined together with the atoms to which they are attached to form a ring having 3 to 6 atoms;

(3) guanidino and substituted guanidino

wherein R° is as defined in 2. (above).

(4) guanyl and substituted guanyl

wherein R° is as defined in 2. (above).

(5) nitrogen-containing mono- and bicyclic heterocyclyls (aromatic and non-aromatic) having 4 to 10 nuclear atoms wherein the hetero atom or atoms, in addition to nitrogen, are selected from oxygen and sulphur. Such heterocyclyls are representatively illustrated by the following list of radicals (R' is H or loweralkyl having 1-6 carbon atoms):

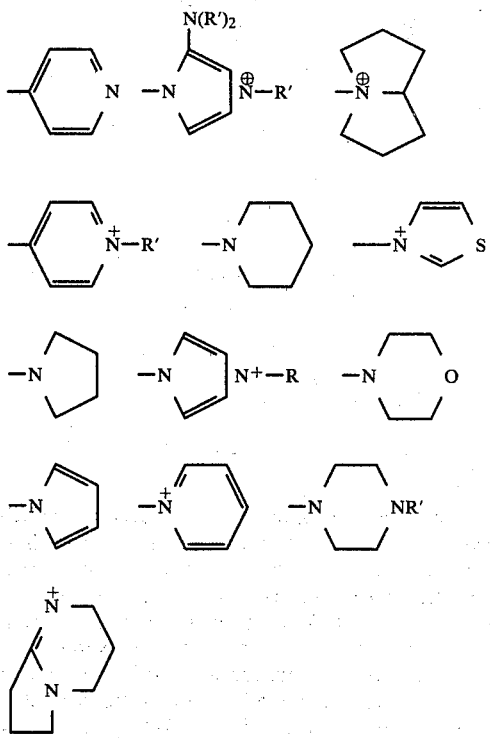

The following specific acyl radicals falling within this class are additionally representative:

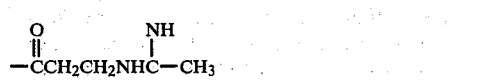

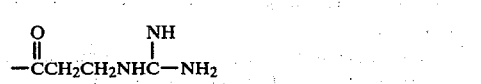

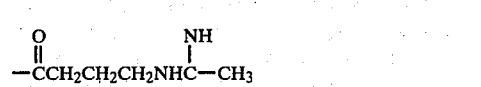

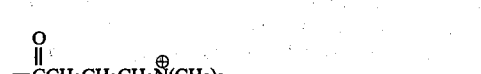

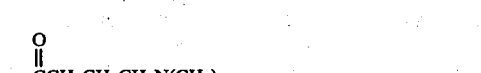

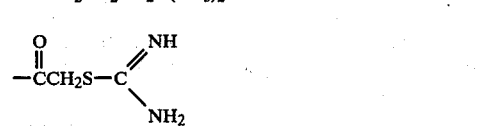

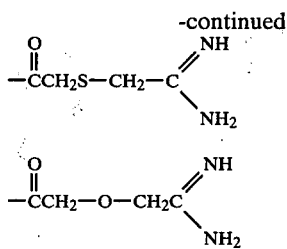

Relative to the generic expression of the compounds of the present invention (Ia):

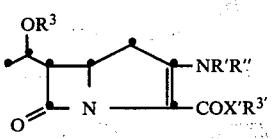

The radicals $R^3$ and/or —$X'R^{3'}$ may be established after synthesis, rather than being established on the starting material 1, by operating upon the hydroxyl group and/or the carboxyl group. Carboxylic acid ester embodiments are conveniently prepared by conventional procedures known in the art. Such procedures include:

(1) Reaction of I in the free acid from with a diazoalkane such as diazomethane, phenyldiazomethane, diphenyldiazomethane and the like in an inert solvent such ad dioxane, THF, halohydrocarbons, acetonitrile, ethylacetate, and the like at a temperature of from $-78°$ C. to 25° C. for from a few minutes to 2 hours.

(2) Reaction of the metallic salts (e.g., Na, Li) of the acid (I) with an activated halide such as methyliodide, benzylbromide, or m-phenoxybenzylbromide, p-t-butylbenzylbromide, m-phenoxybenzylbromide, and the like. Suitable reaction conditions include inert, anhydrous polar non-protic solvents such as hexamethylphosphoramide, DMF, THF, dioxane, and the like at a temperature of from $-78°$ C. to 25° C. for from a few minutes to 4 hours.

(3) Reaction of the free acid (I) with an alcohol such as methanol, ethanol, benzyl alcohol, and the like. This reaction may be conducted in the presence of a carbodiimide condensing agent such as dicyclohexylcarbodiimide or the like. Suitable solvents, at a temperature of from 0° C. to reflux for from 15 minutes to 18 hours, include $CHCl_3$, $CH_3CH$, $CH_2Cl_2$ and the like.

(4) Reaction of an acid anhydride of I, prepared by reacting the free acid (I) with an acid chloride such as ethylchloroformate, benzychloroformate and the like, wtih an alcohol such as those listed in (3) under the same conditions of reaction as given above for (3). The anhydride is prepared by reaction I and the acid chloride in a solvent such as tetrahydrofuran (THF), $CH_2Cl_2$ and the like at a temperature of from 25° C. to reflux for from 15 minutes to 10 hours.

(5) Reaction of labile esters of I such as the trimethylsilyl ester, dimethyl-t-butylsilyl ester or the like with RX' wherein X' is halogen such as bromo and chloro and R is as defined in a solvent such as THF, $CH_2Cl_2$ and the like at a temperature of from 0° C. to reflux for from 15 minutes to 16 hours.

The amides of the present invention are most conveniently prepared by reacting the acid anhydride of I with ammonia or with the amine of choice, e.g., the alkyl-, dialkyl-, aralkyl- or heterocyclic amines listed above.

The above-recited schemes of esterification are well-known in the related bicyclic β-lactam antibiotic art and indeed in all of general organic synthesis as and it is to be noted that there is no undue criticality of reaction parameters in the preparation of the compounds of the present invention.

Establishment of the radical $R^3$ is conveniently established by reacting the carbinol by procedures conventionally known in the art. In general, the compounds of the present invention are prepared by any of a variety of well-known esterification or etherification reactions upon the secondary alcoholic group of I in its protected carboxyl form. Such procedures include:

(1) For the preparation of ether $OR^3$ embodiments of the present invention, the acid catalized reaction of I with a diazoalkane such as diazomethane, phenyldiazomethane, diphenyldiazomethane and the like in an inert solvent such as dioxane, tetrahydrofuran (THF), halohydrocarbons such as $CH_2Cl_2$, ethylacetate and the like in the presence of a catalytic amount of a strong acid or Lewis acid such as toluenesulfonic acid, trifluoroacetic acid, fluoboric acid, boron trifluoride and the like at a temperature of from $-78°$ C. to 25° C. for from a few minutes to 2 hours.

(2) For the preparation of ether $OR^3$ embodiments of the present invention, the reaction of I with an alkylating agent such as active halides, for example, methyliodide, benzylbromide, m-phenoxybenzylbromide, and the like, alkyl sulphonates such as dimethylsulfate, diethylsulphate, methylfluorosulfonate, and the like in the presence of a strong base capable of forming the alcoholate anion of I. Suitable bases include alkali and alkaline earth metal oxides and hydrous oxides, alkali metal alkoxides such as potassium tertiary-butoxide, tertiary amines such as triethylamine, alkali metal alkyls and aryls such as phenyllithium, and alkali metal amides such as sodium amide. Suitable solvents include any inert anhydrous solvent such as t-butanol, dimethylformamide (DMF), THF, hexamethylphosphoramide (HMPA) dioxane and the like at a temperature of from $-78°$ C. to 25° C., for from a few minutes to 4 hours.

(3) For the preparation of ester $OR^3$ embodiments, of the present invention, the reaction of I with any of the above-listed acyl radicals in their acid form. This reaction may be conducted in the presence of a carbodiimide condensing agent such as dicyclohexylcarbodiimide or the like. Suitable solvents include any inert solvent such as $CHCl_3$, $CH_2Cl_2$ DMF, HMPA, acetone, dioxane and the like at a temperature of from 0° C. to 60° C. for from 15 minutes to 12 hours.

(4) For the preparation of ester $OR^3$ embodiments of the present invention, the reaction of I with an acyl halide or an acid anhydride, wherein the acyl moiety is described above. Generally, when the above-described acylating reaction employs an acid halide (suitable halides are chloro, iodo or bromo or acid anhydride) the reaction is conducted in an anhydrous organic solvent such as acetone, dioxane, methylenechloride chloroform, DMF, or the like in the presence of a suitable acceptor base such as $NaHCO_3$, MgO, triethylene, pyridine, and the like at a temperature of from 0° C. to 40° C. for from 1 to 4 hours.

Suitable acyl halides and anhydrides include: acetic anhydride, bromoacetic anhydride, propionic anhydride, benzoylchloride, phenylacetyl chloride, azidoacetyl chloride, 2-thienylacetyl chloride, 2-,3- and 4-nicotinyl chloride, p-nitrobenzoyl chloride, 2,6-dimethoxybenzoyl chloride, 4-guanidinophenylacetyl chloride, hydrochloride, methanesulfonyl chloride, dibenzylphosphorochloridate, dimethylthiophosphorochloridate, 2-furoyl ethyl, 2-furoyl ethyl carbonic anhydride, methylchloroformate, bis(p-nitrobenzyl)phosphorochloridate and the like.

(5) For the preparation of ester $OR^3$ embodiments of the present invention, the reaction of I with a suitably substituted ketene or isocyanate such as ketone, dimethyl ketone, methylisocyanate, methylisothiocyanate, chlorosulfonyl isocyanate and the like. Suitable solvents include dioxane, tetrohydrofuran, chloroform and the like at a temperature of from $-70°$ C. to $60°$ C. for from 15 minutes to 18 hours.

The products of this invention (I) form a wide variety of pharmacologically acceptable salts with inorganic and organic bases; these include, for example, metal salts derived from alkali metal or alkaline earth metal hydroxides, carbonates or bicarbonates and salts derived from primary, secondary or tertiary amines such as monoalkylamines, dialkylamines, trialkylamines, lower alkanolamines, di-lower-alkanolamines, lower alkylenediamines, N,N-diaralkyl lower alkylenediamines, aralkylamines, amino substituted lower alkanols, N,N-di-lower alkylamino substituted lower alkanols, amino-, polyamino- and guanidino-substituted lower alkanoic acids and nitrogen containing heterocyclic amines. Representative of such salts are sodium, potassium, and calcium salts and amine salts such as benzhydrylamine, N-benzyl-2-phenethylamine, N,N'-dibenzylethylenediamine, and procaine salts.

The salts of this invention are pharmacologically acceptable non-toxic derivatives which can be used as the active ingredient in suitable unit dosage pharmaceutical forms. Also, they may be combined with other drugs to provide compositions having a broad spectrum of activity.

The novel compounds are valuable antibiotics active against various gram-positive and gram-negative bacteria and, accordingly, find utility in human and veterinary medicine. The compounds of this invention can therefore be used as antibacterial drugs for treating infections caused by gram-positive or gram-negative bacteria, for example, against *Staphylococcus aureus, Escherichia coli, Klebsiella pneumoniae, Serratia, Salmonella typhosa,* Pseudomonas and *Bacterium proteus.* The antibacterials of the present may further be utilized as additives to animal feeding stuffs, for preserving foodstuffs and as disinfectants. For example, they may be employed in aqueous compositions in concentrations ranging from 0.1 to 100 parts of antibiotic per million parts of solution in order to destroy and inhibit the growth of harmful bacteria on medical and dental equipment and as bactericides in industrial applications, for example, in waterbased pains and in the white water of paper mills to inhibit the growth of harmful bacteria.

The products of this invention may be used alone or in combination as an active ingredient in any one of a variety of pharmaceutical preparations. These antibiotics and their corresponding salts may be employed in capsule form or as tablets, powders or liquid solutions or as suspensions or elixirs. They may be administered orally, intravenously or intramuscularly.

The compositions are preferably presented in a form suitable for absorption by the gastro-intestinal tract. Tablets and capsules for oral administration may be in unit dose presentation form, and may contain conventional excipients such as binding agents, for example, syrup, acacia, gelatin, sorbitol, tragacanth, or polyvinylpyrrlidone; fillers for example, lactose, sugar, maizestarch, calcium phosphate, sorbitol or glycine; lubricants, for example, magnesium stearate, talc, polyethylene glycol, silica; disintegrants, for example, potato starch or acceptable wetting agents such as sodium lauryl sulphate. The tablets may be coated according to methods well known in the art. Oral liquid preparations may be in the form of aqueous or oily suspension, solution, emulsions, syrups, elixirs, etc. or may be presented as a dry product, for reconstitution with water or other suitable vehicles before use. Such liquid preparations may contain conventional additives such as suspending agents, for example, sorbitol syrup, methyl cellulose, glucose/sugar syrup, gelatin, hydroxyethylcellulose, carboxymethyl cellulose, aluminum stearate gel or hydrogenated edible oils, for example almond oil, fractionated coconut oil, oily esters, propylene glycol, or ethyl alcohol; preservatives, for example methyl or propyl p-hydroxybenzoates or sorbic acid. Suppositories will contain conventional suppository bases, e.g., cocoa butter or other glyceride.

Compositions for injection may be presented in unit dose form in ampules, or in multidose containers with an added preservative. The compositions may take such forms as suspensions, solutions, or emulsions in oily or aqueous vehicles, and may contain formulatory agents such as suspending, stabilizing and/or dispersing agents. Alternatively, the active ingredient may be in powder form for reconstitution with a suitable vehicle, e.g., sterile, pyrogen-free water, before use.

The compositions may also be prepared in suitable forms for absorption through the mucous membranes of the nose and throat or bronchial tissues and may conveniently take the form of powder or liquid sprays or inhalants, lozenges, throat paints, etc. For medication of the eyes or ears, the preparations may be presented as individual capsules, in liquid or semi-solid form, or may be used as drops etc. Topical applications may be formulated in hydrophobic or hydrophilic bases such as ointments, creams, lotions, paints, powders, etc.

Also, in addition to a carrier, the instant compositions may include other ingredients such as stabilizers, binders, antioxidants, preservatives, lubricators, suspending agents, viscosity agents or flavoring agents and the like. In addition, there may also be included in the composition other active ingredients to provide a broader spectrum of antibiotic activity.

For veterinary medicine the composition may, for example, be formulated as an intramammary preparation in either long or quick-release bases.

The dosage to be administered depends to a large extent upon the condition of the subject being treated and the weight of the host, the route and frequency of administration, the parenteral route being preferred for generalized infections and the oral route for intestinal infections. In general, a daily oral dosage consists of from about 2 to about 600 mg. of active ingredient per kg. of body weight of the subject in one or more applications per day. A preferred daily dosage for adult humans lies in the range of from about 15 to 150 mg. of active ingredient per kg. of body weight.

The instant compositions may be administered in several unit dosage forms as, for example, in solid or liquid orally ingestible dosage form. The compositions per unit dosage, whether liquid or solid may contain from 0.1% to 99% of active material, the preferred range being from about 10–60%. The composition will generally contain from about 15 mg. to about 1500 mg.

of the active ingredient; however, in general, it is preferable to employ a dosage amount in the range of from about 100 mg. to 1000 mg. In parenteral administration the unit dosage is usually the pure compound in a slightly acidified sterile water solution or in the form of a soluble powder intended for solution.

The following Examples, illustrate but do not limit the product, process, compositional or method of treatment aspects of the present invention. All temperatures are in °C.

EXAMPLE 1

Preparation of 4-(2-Acetoxyethyl)-azetidin-2-one

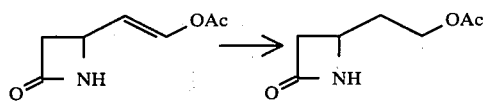

A mixture of 4-(2-acetoxyvinyl)-azetidin-2-one (3.00 g), 10% Pd/C (0.15 g) and ethylacetate(EtOAc) (120 ml) is hydrogenated in a 500 ml glass bomb on a Parr shaker at an initial pressure of 39 psi. After shaking 10 mins (final pressure of 20 psi), the mixture is filtered through a pad of MgSO4 to remove the catalyst. The filtrate is concentrated in vacuo and the residue stripped with anhydrous benzene to provide 4-(2-acetoxyethyl)-azetidin-2-one (3.098 g) as a clear oil: ir(neat) 3.01, 5.66, 5.75, 7.28, 8.05, and 9.61 cm$^{-1}$; nmr(CDCl$_3$) δ1.95 (m, 2), 2.07 (s, 3), 2.60 (m, 1), 3.12 (m, 1), 3.70 (m, 1), 4.15 (m, 2), and 6.77 (br s, 1).

EXAMPLE 2

Preparation of N-(t-Butyldimethylsilyl)-4-(2-acetoxyethyl)azetidin-2-one

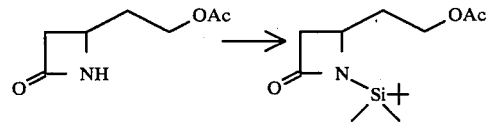

Triethylamine (Et$_3$N) (2.96 ml, 21.2 mmol) and t-butyldimethylsilyl chloride (3.059 g, 20.3 mmol) are added to an ice-cold stirring solution of 4-(2-acetoxyethyl)-azetidin-2-one (3.098 g, 19.3 mmol) in anhydrous dimethylformamide(DMF) (20 ml). A white precipitate appears immediately. The cooling bath is removed and the mixture is stirred at 25° C. (room temperature) for 5 mins. The mixture is diluted with benzene (200 ml), washed with H$_2$O (5×80 ml) and brine, dired with MgSO$_4$, filtered, and evaporated under reduced pressure to afford N-(t-butyldimethylsilyl)-4-(2-acetoxyethyl)-azetidin-2-one (5.078 g) as an off white solid: ir(-neat) 5.75, 8.08, 8.41, 11.92, and 12.18 cm$^{-1}$; nmr (CDCl$_3$) δ0.25 (s, 6), 0.98 (s, 9), 1.97 (m, 2), 2.05 (s, 3), 2.67 (dd, 1), 3.20 (dd, 1) 3.62 (m, 1), and 4.12 (t, 2); mass spectrum m/e 214 (M$^+$-57) and 172.

EXAMPLE 3

Preparation of N-(t-Butyldimethylsilyl)-4-(2-hydroxyethyl)-azetidin-2-one

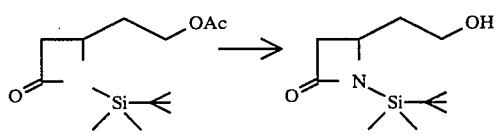

A solution of N-(t-butyldimethylsilyl)-4-(2-acetoxyethyl)-azetidin-2-one (41.7 g, 0.154 mol) in anhydrous methanol (415 ml) is stirred under a N$_2$ atmosphere with ice-bath cooling. A solution of sodium methoxide (415 mg, 7.7 mmol) in anhydrous methanol (15 ml) is added and the resulting solution is stirred in the cold for 2 more hrs. Acetic acid (2.2 ml) is then added and the solvents are evaporated in vacuo (i.v.). The residue is taken up in EtOAc (300 ml), washed with H$_2$O (4×75 ml), 5% NaHCO$_3$ (75 ml) and brine, dried with MgSO$_4$ and evaporated i.v. to a clear oil (21.3 g). This material is purified by chromatography on a Baker silica gel column (425 g, packed under EtOAc). After a 100 ml forefraction, 25 ml EtOAc fractions are collected every 2.5 mins. Fractions 41-49 yield starting material and fractions 51-90 afford N-(t-butyldimethylsilyl)-4-(2-hydroxyethyl)-azetidin-2-one (19.4 g) as a clear oil: ir (neat) 2.88, 5.73, 5.80, 7.52, 7.67, 7.99, 8.40, 11.95, and 12.18 cm$^{-1}$; nmr (CDCl$_3$) δ0.25 (s, 6), 0.98 (s, 9), 1.82 (m, 2), 2.67 (dd, 1), 3.17 (dd, 1), 3.67 (t, 2), and 3.67 (m,1); mass spectrum m/e 172.

EXAMPLE 4

Preparation of N-(t-Butyldimethylsilyl)-4-(2-oxoethyl)-azetidin-2-one

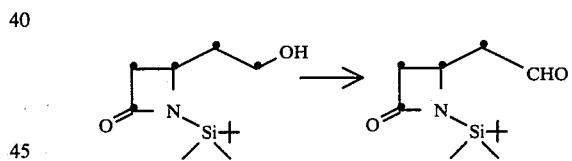

Anhydrous chromium trioxide (CrO$_3$) (1.94 g, 19.4 mmol) is added to a solution of anhydrous pyridine (3.07 g, 38.8 mmole) in anhydrous methylene chloride (CH$_2$Cl$_2$) (50 ml). The resulting mixture is stirred at room temperature for 15 mins. A solution of N-(t-butyl-dimethylsilyl)-4-(2-dihydroxyethyl)-azetidin-2-one (0.74 g, 3.23 mmol) in anhydrous CH$_2$Cl$_2$ (5 ml) is added all at once. After stirring at room temperature for 5 mins, the mixture is decanted and the dark, gummy residue is washed with more CH$_2$Cl$_2$. The combined CH$_2$Cl$_2$ supernatant is evaporated i.v. The residue is tabken up in diethyl ether and filtered to remove chromium salts. The ethereal filtrate is washed with 5% NaHCO$_3$, 5% HCl, 5% NaHCO$_3$ and brine, dried with MgSO$_4$, filtered, and evaporated i.v. to yield N-(t-butyl-dimethylsilyl)-4-(2-oxoethyl)-azetidin-2-one (0.54 g) as an off-white solid: ir(CHCl$_3$) 5.77, 5.80, 7.36, 7.60, 7.99, 8.50 and 11.95 cm$^{-1}$; nmr (CDCl$_3$) δ0.23 (s, 3), 0.27 (s, 3), 0.98 (s, 9), 2.63 (ddd, 1), 2.65 (dd, 1), 3.07 (ddd, 1), 3.37 (dd), 3.97 (m, 1), and 9.78 (t, 1); mass spectrum m/e 170 and 128.

EXAMPLE 5

Preparation of
N-(t-Butyldimethylsilyl)-4-(3-benzyloxycarbonyl-2-hydroxypropyl)-azetidin-2-one

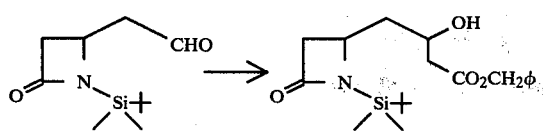

To a flame dried, 50 ml, 3-neck flask fitted with a N$_2$ inlet, magnetic stirrer, addition funnel, and serum cap are added anhydrous tetrahydrofuran (THF) (10.5 ml) and diisopropyl amine (0.579 ml, 4.13 mmol). The solution is cooled in an ice-methanol bath under N$_2$ and treated with 2.4 N n-butyl lithium in hexane (1.72 ml). After being stirred at $-10°$ for 15 mins, the solution is cooled to $-78°$ and treated dropwise over 9 mins with a solution of benzyl acetate (0.620 g, 4.13 mmol) in anhydrous THF (3.5 ml). After stirring 15 more mins at $-78°$ C., the reaction mixture is treated dropwise over 13 mins with a solution of N-(t-butyldimethylsilyl)-4-(2-oxoethyl)-azetidin-2-one (0.894 g, 3.93 mmol) in anhydrous THF (6 ml). The reaction mixture is stirred at $-78°$ an additional 15 mins and then quenched with 2.5 N HCl (6 ml). EtOAc (100 ml) is added and the oragnic phase is separated, washed with H$_2$O (2×20 ml), 5% NaHCO$_3$ (20 ml) and brine, dried with MgSO$_4$, and filtered. The filtrate is evaporated i.v. and the residue stripped with φH to yield N-(t-butyldimethylsilyl)-4-(3-benzyloxycarbonyl-2-hydroxypropyl)-azetidin-2-one (1.432 g) as an oil: ir (neat) 2.87, 5.73, 5.79, 7.57, 7.96, 8.39, 11.92, and 12.16 cm$^{-1}$; mass spectrum m/e 362, 320, 278, 170 and 128.

EXAMPLE 6

Preparation of
N-(t-Butyldimethylsilyl)-4-(3-benzyloxycarbonyl-2-oxopropyl)-azetidin-2-one

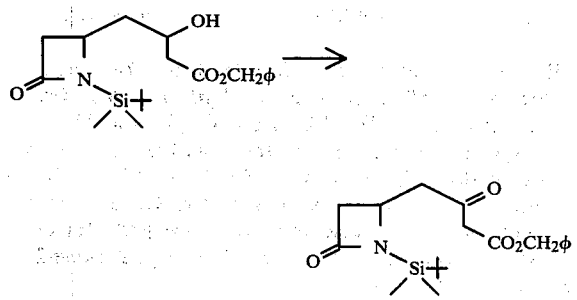

Anhydrous CrO$_3$ (2.274 g, 22.74 mmol) is added to a solution of anhydrous pyridine (3.597 g, 45.48 mmol) in anhydrous CH$_2$Cl$_2$ (60 ml). After stirring at room temperature (25° C.) for 15 mins, the reaction mixture is treated all at once with a solution of N-(t-butyldimethylsilyl)-4-(3-benzyloxycarbonyl-2-hydroxypropyl)-azetidin-2-one (1.432 g, 3.79 mmol) in anhydrous CH$_2$Cl$_2$ (25 ml). The resulting mixture is stirred at 25° C. for 5 mins. The CH$_2$Cl$_2$ layer is decanted from the dark, gummy residue which is triturated with more CH$_2$Cl$_2$. The combined CH$_2$Cl$_2$ phase is evaporated i.v. The residue is triturated with diethylether (Et$_2$O) (100 ml) in several portions and the Et$_2$O extracts are filtered to remove chromium salts. The ethereal filtrate is washed with 5% NaHCO$_3$, 1 N HCl, 5% NaHCO$_3$ and brine, dried with MgSO$_4$, filtered, and evaporated i.v. to yield N-(t-butyldimethylsilyl)-4-(3-benzyloxycarbonyl-2-oxopropyl)-azetidin-2-one (1.042 g) as a pale yellow oil: ir (neat) 5.72 (3 poorly resolved peaks), 7.59 7.98, 8.42, and 11.93 cm$^{-1}$; nmr (CDCl$_3$) δ0.18 (s, 3), 0.22 (s, 3), 0.97 (s, 9), 2.53 (dd, 1), 2.63 (dd, 1), 3.13 (dd, 1), 3.28 (dd, 1), 3.47 (s,2), 3.88 (m, 1), 5.17 (s, 2), and 7.33 (s, 5); mass spectrum m/e 360, 318, and 2.76.

EXAMPLE 7

Preparation of
4-(3-Benzyloxycarbonyl-2-oxopropyl)azetidin-2-one

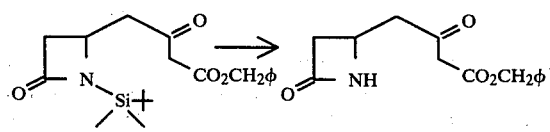

N-(t-butyldimethylsilyl)-4-(3-benzyloxycarbonyl-2-oxopropyl)-azetidin-2-one (302 mg, 0.80 mmol) is dissolved in acetic acid (4.0 ml) and the solution is diluted with H$_2$O(2.0 ml). The resulting solution is stirred in a securely stoppered, 10 ml, round-bottom flask in an oil bath maintained at 73° C. for 7 hrs. After cooling to room temperature, the reaction mixture is diluted with EtOAc and toluene and evaporated i.v. The residue is stripped twice with toluene to yield a yellow oil (220 mg). The crude product is chromatographed on Baker silica gel (8.8 g, packed under EtOAc). The column is eluted with EtOAc; 3 ml fractions being collected every 2.25 mins. Fractions 14–30 are combined and evaporated i.v. to provide 4-(3-benzyloxycarbonyl-2-oxopropyl)azetidin-2-one (114 mg) as a clear oil: ir (neat) 3.04, 5.68, 5.72 and 5.83 cm$^{-1}$; nmr (CDCl$_3$) δ2.52 (ddd, 1), 2.67 (dd, 1), 3.02 (dd, 1), 3.12 (ddd, 1), 3.48 (s, 2), 3.88 (m, 1), 5.18 (s, 2), 6.17 (m, 1), and 7.37 (s, 5); mass spectrum m/e 261 (M+), 233, 219, 192, 127 and 91.

EXAMPLE 8

Preparation of
4-(3-Benzyloxycarbonyl-3-diazo-2-oxopropyl)-azetidin-2-one

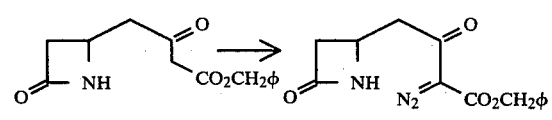

Freshly recrystallized p-carboxy benzene sulfonylazide (241 mg, 1.06 mmol) is added to a solution of 4-(3-benzyloxycarbonyl-2-oxopropyl)-azetidin-2-one (276 mg, 1.06 mmol) in anhydrous acetonitrile (6.6 ml). The resulting suspension is cooled in an ice-bath and stirred while Et$_3$N (443 μl, 3.18 mmol) is added. The resulting yellow solution is stirred at room temperature. A precipitate forms quickly. After 90 mins, the mixture is diluted with EtOAc (50 ml) and filtered. The filtrate is washed with H$_2$O (2×10 ml), 0.5 N NaOH (2×10 ml), H$_2$O (4×10 ml) and brine, dried with MgSO$_4$, filtered, and evaporated i.v. to an off-white solid (273 mg). This is triturated with Et$_2$O to provide 4-(3-benzyloxycarbonyl-3-diazo-2-oxopropyl)-azetidin-2-one (227 mg) as a cream colored powder: ir (film from CHCl3) 3.0, 4.65, 5.66, 5.82, 6.05, 7.21, 7.70 and 8.23 cm$^{-1}$; nmr (CDCl3) δ2.63 (ddd,1), 2.97 (dd, 1), 3.15 (ddd, 1), 3.40 (dd, 1), 3.98 (m, 1), 5.27 (s, 2), 6.13 (m, 1), and 7.38 (s, 5); mass spectrum m/e 259, 245, 231, and 218.

EXAMPLE 9

Preparation of Benzyl 1-azabicyclo[3.2.0]heptan-3,7-dione-2-carboxylate

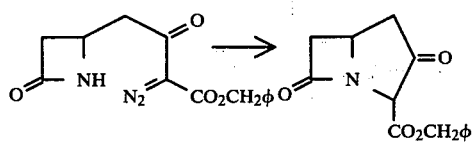

A solution of 4-(3-benzyloxycarbonyl-3-diazo-2-oxopropyl)-azetidin-2-one (20 mg) in anhydrous benzene (5 ml) is irradiated for 60 mins at room temperature using a Hanovia 450 W medium-pressure mercury lamp and a Pyrex filter. Dry N2 is bubbled through the solution prior to and during the photolysis. Evaporation of the solvent in vacuo gives an oil (17 mg) which is purified by chromatography on a 250μ×20×20 cm silica gel GF plate using 3:1 φH-EtOAc as developing solvent. The band at Rf 0.3 is removed and eluted with EtOAc to give a clear oil (2.4 mg). This material is further purified by tlc on a 250μ×7.5×8.5 cm silica gel GF plate. The cleanly resolved band at Rf 0.29 is removed and eluted with EtOAc to give benzyl 1-azabicyclo[3.2.0]heptan-3,7-dione-2-carboxylate (0.7 mg) as a clear oil: ir (CCl4) 1783, 1773, and 1744 cm$^{-1}$; ir (CHCl3) 1767, 1741 cm$^{-1}$; uv (Cy) 215 nm; nmr (CDCl3) δ2.36 (dd, J=8 and 18.5, 1) 2.90 (dd, J=6 and 18.5, 1), 2.92 (dd, J=2 and 16, 1), 3.63 (dd, J=5 and 16, 1), 4.11 (m, 1), 4.71 (s, 1), 5.19 (s, 2) and 7.33 (s, 5); mass spectrum m/e 259 (M+), 231 (M+−28), 217 (M+−42), 203, 187, 186, 168 (M+−91), 124, and 91; high resolution mass spectrum m/e 259.0842 (C14H13NO4).

EXAMPLE 10

Preparation of Benzyl 3-toluenesulfonyloxy-1-azabicyclo[3.2.0]hept-2-en-7-one-2-carboxylate

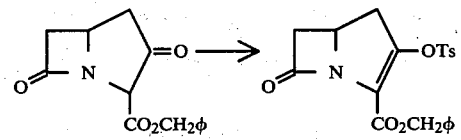

p-Toluenesulfonic anhydride (33 mg, 0.1 mmol) and Et3N (17 μl, 0.12 mmol) are added to a solution of benzyl 1-azabicyclo[3.2.0]heptan-3,7-dione-2-carboxylate (26 mg., 0.1 mmol) in anhydrous CH2Cl2 (2 ml). The resulting solution is stirred at room temperature for 2 hours. The mixture is diluted with CH2Cl2 (10 ml), washed with H2O (2×5 ml), pH 3 phosphate buffer (5 ml) and 5% NaHCO3 (5 ml), dried with MgSO4, filtered and evaporated i.v. to provide benzyl 3-toluenesulfonyloxy-1-azabicyclo[3.2.0]hept-2-en-7-one-2-carboxylate.

EXAMPLE 11

Preparation of Benzyl 6-(1-hydroxyethyl)-3-toluenesulfonyloxy-1-azabicyclo[3.2.0]hept-2-en-7-one-2-carboxylate

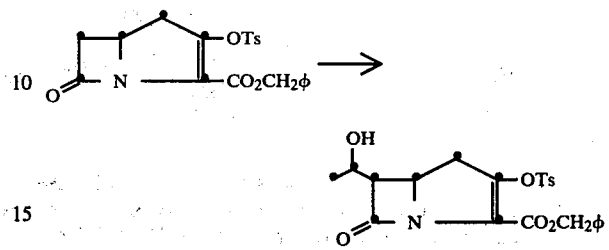

A solution of benzyl 3-toluenesulfonyloxy-1-azabicyclo[3.2.0]hept-2-en-7-one-2-carboxylate (41 mg) in anhydrous THF (0.5 ml) is added dropwise over 5 mins to a stirring solution of lithium diisopropylamide (from 15.5 μl of diisopropylamine and 0.07 ml of 1.6 N BuLi) in anhydrous THF (1.5 ml) at −78°. The resulting solution is stirred at −78° for 10 mins and then treated with acetaldehyde (56 μl). After 5 more mins, saturated aqueous NH4Cl solution (1.5 ml) is added and the mixture is allowed to warm to room temperature. The mixture is diluted with ethyl acetate (20 ml), washed with H2O and brine, dried with MgSO4, filtered, and evaporated in vacuo to provide benzyl 6-(1-hydroxyethyl)-3-toluenesulfonyloxy-1-azabicyclo[3.2.0]hept-2-en-7-one-2-carboxylate as a mixture of diastereomers.

EXAMPLE 12

Preparation of Benzyl 3-chloro-1-azabicyclo[3.2.0]hept-2-en-7-one-2-carboxylate

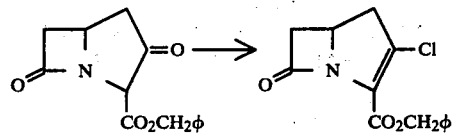

Benzyl 1-azabicyclo[3.2.0]heptane-3,7-dione-2-carboxylate 26 mg, 0.1 mmol) in anhydrous DMF (0.5 ml) containing PCl3 (27 mg, 0.2 mmol) is kept at 25° C. for 5 hours. The mixture is diluted with toluene (5 ml), washed with H2O (5×1 ml), 5% HCl (2 ml), 5% NAHCO3 (2 ml) and brine, dried with MgSO4, and filtered. Evaporation of the solvent in vacuo provides crude benzyl 3-chloro-1-azabicyclo[3.2.0]hept-2-en-7-one-2-carboxylate.

EXAMPLE 13

Preparation of Benzyl 6-(1-hydroxyethyl)-3-chloro-1-azabicyclo[3.2.0]hept-2-en-7-one-2-carboxylate

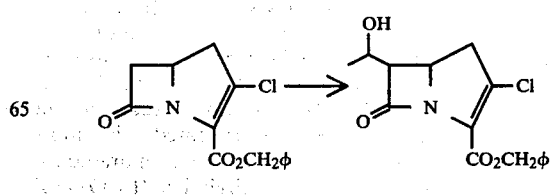

The title compound is obtained by the procedure of Example 11 by substituting benzyl 3-chloro-1-azabicyclo[3.2.0]hept-2-en-7-one-2-carboxylate (28 mg) for the 3-toluenesulfonyloxy derivative.

EXAMPLE 14

Preparation of Benzyl 6-(1-hydroxyethyl)-3-propylamino-1-azabicyclo[3.2.0-]hept-2-en-7-one-2-carboxylate

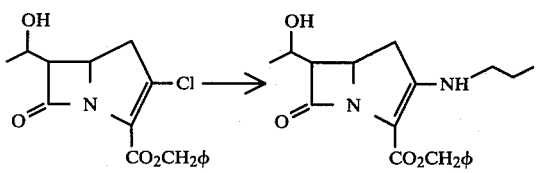

A solution of benzyl 6-(1-hydroxyethyl)-3-chloro-1-azabicyclo[3.2.0]hept-2-en-7-one-2-carboxylate (48 mg) in anhydrous DMF (1 ml) is cooled in an ice bath and stirred while triethylamine (28 μl) and propylamine (12.4 μl) are added. The resulting solution is allowed to warm to room temperature (25° C.) and kept there for 1 hour. The solution is diluted with ethyl acetate (10 ml), washed with water (5×2 ml), pH 3 phosphate buffer (2 ml), 5% NaHCO3 (2 ml), and brine, dried with MgSO4, filtered, and evaporated in vacuo to provide benzyl 6-(1-hydroxyethyl)-3-propylamino-1-azabicyclo[3.2.0-]hept-2-en-7-one-2-carboxylate.

EXAMPLE 15

Preparation of Sodium 6-(1-hydroxyethyl)-3-propylamino-1-azabicyclo[3.2.0-]hept-2-en-7-one-2-carboxylate

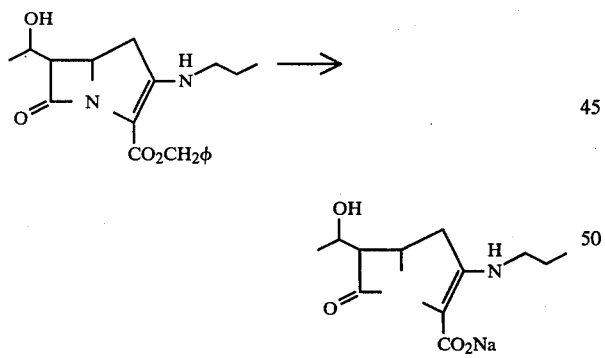

Benzyl 6-(1-hydroxyethyl)-3-propylamino-1-azabicyclo[3.2.0]hept-2-en-7-one-2-carboxylate (30 mg) is dissolved in dioxane (2 ml) and water (1 ml) containing sodium bicarbonate (7.5 mg). 10% palladium on powdered charcoal (30 mg) is added and the resulting mixture is hydrogenated at 40 psi for 1 hr. The catalyst is filtered off and washed with water (3 ml). The combined filtrate is extracted with ethyl acetate (3×2 ml), conc. in vacuo, and lyophilized to afford sodium 6-(1-hydroxyethyl)-3-propylamino-1-azabicyclo[3.2.0]hept-2-en-7-one-2-carboxylate.

EXAMPLE 16

Preparation of Benzyl 6-(1-hydroxyethyl)-3-morpholino-1-azabicyclo[3.2.0-]hept-2-en-7-one-2-carboxylate

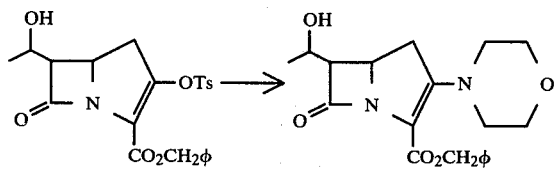

Morpholine (17.5 μl) is added to an ice-cold, stirring solution of benzyl 6-(1-hydroxyethyl)-3-toluenesulfonyloxy-1-azabicyclo[3.2.0]hept-2-en-7-one-2-carboxylate (46 mg) in anhydrous DMF (1 ml). The resulting solution is brought to room temperature and kept at that temperature for 4 hrs. The solution is diluted with ethyl acetate (10 ml), washed with water (5×2 ml), pH 3 phosphate buffer (2 ml), 5% NaHCO3 (2 ml), and brine, dried with MgSO4, filtered, and evaporated in vacuo to give benzyl 6-(1-hydroxyethyl)-3-morpholine-1-azabicyclo[3.2.0]hept-2-en-7-one-2-carboxylate.

EXAMPLE 17

Preparation of Sodium 6-(1-hydroxyethyl)-3-morpholino-1-azabicyclo[3.2.0-]hept-2-en-7-one-2-carboxylate

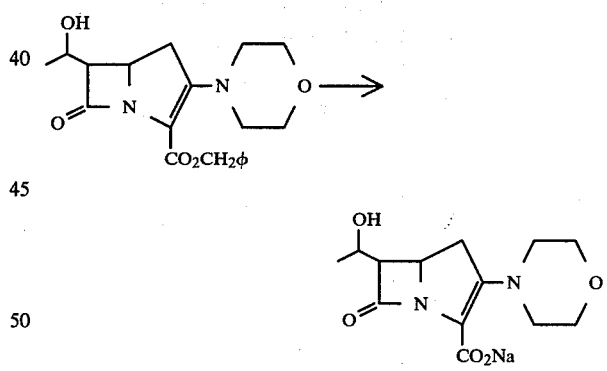

A solution of benzyl 6-(1-hydroxyethyl)-3-morpholino-1-azabicyclo[3.2.0]hept-2-en-7-one-2-carboxylate (30 mg) in dioxane (3 ml) is diluted with water (1 ml) containing sodium bicarbonate (7 mg). 10% palladium on powdered charcoal (30 mg) is also dried and the resulting mixture is hydrogenated at 40 psi for 30 mins. The catalyst is filtered off and washed with water (3×3 ml). The combined filtrate is extracted with ethyl acetate (3×2 ml), concentrated in vacuo to ca. 2 ml, and lyophilized to give sodium 6-(1-hydroxyethyl)-3-morpholino-1-azabicyclo[3.2.0]hept-2-en-7-one-2-carboxylate.

EXAMPLE 18

Preparation of Benzyl 6-(1-hydroxyethyl)-3-[N-methyl-N-(2-dimethylaminoethyl)aminol-1-azabicyclo[3.2.0]hept-2-en-7-one-2-carboxylate

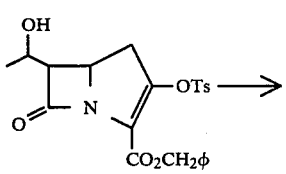

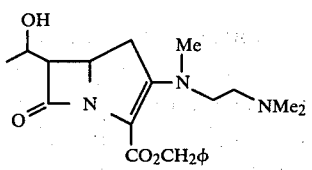

A mixture of benzyl 6-(1-hydroxyethyl)-3-toluenesulfonyloxy-1-azabicyclo[3.2.0]hept-2-en-7-one-2-carboxylate (46 mg) N-methyl-N-(2-dimethylaminoethyl)amine (10.2 mg), and triethylamine (28 μl) in anhydrous DMF (0.5 ml) is stirred at room temperature for 4 hrs. The mixture is diluted with ethyl acetate (10 ml) washed with H₂O (5×2 ml) and brine, dried with MgSO₄, filtered and evaporated in vacuo to provide benzyl 6-(1-hydroxyethyl)-3-[N-methyl-N-(2-dimethylaminoethyl)amino]-1-azabicyclo[3.2.0]hept-2-en-7-one-2-carboxylate.

EXAMPLE 19

Preparation of 6-(1-hydroxyethyl)-3-[N-methyl-N-(2-dimethylaminoethyl)amino]-1-azabicyclo[3.2.0]hept-2-en-7-one-2-carboxylic acid

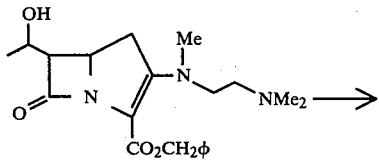

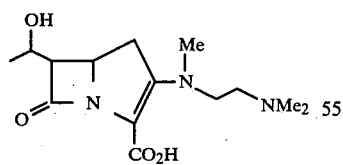

A mixture of benzyl 6-(1-hydroxyethyl)-3-[N-methyl-N-(2-dimethylaminoethyl)amino]-1-azabicyclo[3.2.0]hept-2-en-7-one-2-carboxylate (25 mg), 10% palladium on powdered charcoal (25 mg), dioxane (3 ml), water (1.5 ml), and ethanol (0.5 ml) is hydrogenated at 45 psi for 1 hr. The catalyst is filtered off and washed with H₂O (5 ml). The combined filtrate is extracted with ethyl acetate, concentrated in vacuo to ca. 1 ml, and lyophilized to yield the title compound.

EXAMPLE 20

BENZYL 1-AZABICYCLO[3.2.0]HEPTAN-3,7-DIONE-2-CARBOXYLATE

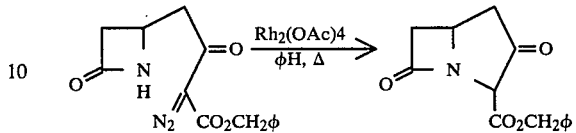

A mixture of 4-(3-benzyloxycarbonyl-3-diazo-2-oxopropyl)-azetidin-2-one (718 mg. 2.5 mMol), rhodium (II) acetate (5 mg) and anhydrous benzene (50 ml) is deoxygenated by bubbling nitrogen through it for 45 minutes. The mixture is then stirred and heated in an oil bath maintained at 80° C. for 70 minutes. After cooling to room temperature, the mixture is filtered and the filtrate is evaporated under vacuum to an oil. Crystallization from ethyl acetate (5 ml)-diethylether (20 ml) provides benzyl 1-azabicyclo[3.2.0]heptan-3,7-dione-2-carboxylate (502 mg, 77% yield) as small, white prisms: mp 100°–102°; IR (CH₂Cl₂) 1770; 1741 cm⁻¹; UV (dioxane) 220 nm; NMR (CDCl₃, 300 MHz) α2.43 (dd,1,J=8 and 19, H4a), 2.94 (dd,1,J=6.5 and 19, H4b), 2.99 (dd,1,J=2 and 16, H6B), 3.63 (dd,1,J=5 and 16, H6α), 4.18 (m,1,H5), 4.76 (S,1,H2), 5.23 (S,2,CH₂φ), and 7.40 (S,5,ArH); MS m/e 259 (M+), 231 (M+ −28), 217 (M+ −42), 203, 187, 186, 168 (M+ −91), 124, and 91.

Anal. Calculated for C₁₄H₁₃NO₄: C, 64.86; H, 5.05; N, 5.40. Found: C, 64.92; H, 5.01; N, 5.11.

EXAMPLE 21

DICYCLOHEXYLAMMONIUM 1-AZABICYCLO[3.2.0]HEPTAN-3,7-DIONE-2-CARBOXYLATE

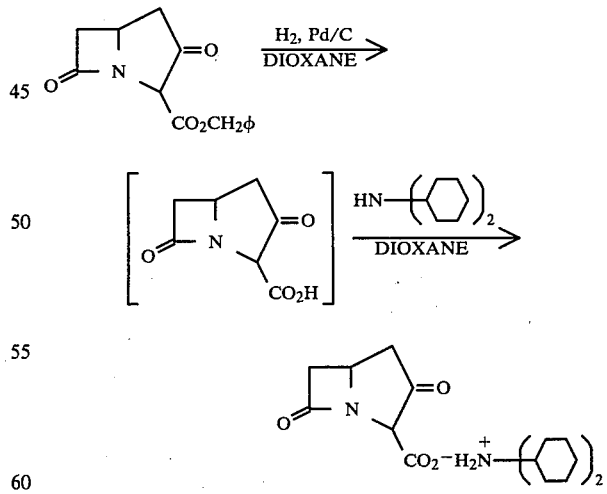

A solution of benzyl 1-azabicyclo[3.2.0]heptan-3,7-dione-2-carboxylate (25.9 mg, 0.1 mMol) in dioxane (1.5 ml) is added to a mixture of 10% palladium on charcoal (5 mg) and dioxane (1.0 ml) which had been equilibrated under an atmosphere of hydrogen for 10 minutes. The resulting mixture is stirred under 1 atmosphere of hydrogen at room temperature for 30 mins., during which time 2.6 ml of hydrogen are absorbed. The mixture is filtered and the catalyst is washed with more dioxane (0.5 ml). The filtrate, which contains 1-azabicyclo[3.2.0-]heptan-3,7-dione-2-carboxylic acid, is divided into two equal 1.5 ml portions.

One portion of the dioxane filtrate is treated with a solution of dicyclohexylamine (9.1 mg, 0.05 mMol) in dioxane. The solvent is removed under vacuum and the residue is triturated with diethyl ether to yield dicyclohexylammonium 1-azabicyclo[3.2.0]heptan-3,7-dione-2-carboxylate as a white powder; IR (Nujol) 1764, 1637 cm$^{-1}$; NMR (D$_2$O) $\alpha$ 1.1–2.2 (m,—CH$_2$CH$_2$CH$_2$CH$_2$CH$_2$—), 2.64 (dd,J=7.8 and 19.0, H4a), 2.89 (dd, J=7.9 and 19.0, H4b), 3.08 (dd, J=2 and 16.6, H6$\beta$), 3.26 (m, N—CH), 3.61 (dd, J=4.7 and 16.6, H6$\alpha$), 4.17 (m, H5), and 4.8 (br s, HOD, obscures H2 resonance).

EXAMPLE 22

Benzyl 3-(p-toluenesulfonyloxy)-1-azabicyclo[3.2.0]hept-2-2n-7-one-2-carboxylate

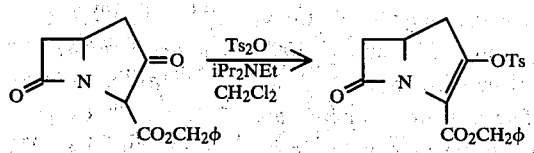

p-Toluenesulfonic anhydride (326 mg, 1 m$\mu$ol) and N,N-diisopropylethylamine (192 $\mu$l, 1.1 m$\mu$ol) are added to an ice-cold, stirring solution of benzyl 1-azabicyclo[3.2.0]heptan-3,7-dione-2-carboxylate (259 mg, 1 m$\mu$ol) in anhydrous methylene chloride (10 ml). The resulting solution is stirred in the cold and under a nitrogen atmosphere for 2.5 hours. The solution is diluted with methylene chloride (20 ml), washed with water (10 ml). 1 M pH3 phosphate buffer (10 ml) and 5% aqueous sodium bicarbonate (2×10 ml) dried with magnesium sulfate, filtered, and evaporated under vacuum to a semi-solid. This material is triturated with ice-cold ethyl acetate (2×2 ml) and diethyl ether (2×5 ml) to provide benzyl 3-(p-toluenesulfonyloxy)-1-azabicyclo[3.2.0]hept-2-en-7-one-2-carboxylate (276 mg, 67%) as a white powder. Recrystallization from methylene chloride-diethyl ether gives analytically pure product as small white needles: mp 103°–105°; IR (CH$_2$Cl$_2$) 1786, 1723, 1382, and 1190 cm$^{-1}$; NMR (CDCl$_3$) δ 2.44 (s,3,ArCh$_3$) 3.03 (dd,1,J=3.0 and 17.0, HG$\beta$), 3.16 (dd,1,J=8.5 and 18.7,H4a), 3.32 (dd,1,J=10.0 and 18.7,H46), 3.55 (dd,1,J=5.5 and 17.0, HG), 4.21 (m,1,H5), 5.14 (ABq,2,J=12,CH$_2$Ar), 7.35 (S,5,ArHO, 7.26 and 7.75 (two d's,4,J=9,ArH); UV(dioxane) 283 (E6600) and 277 (E6500) nm.

Anal., Calculated for C$_{21}$H$_{19}$NO$_6$S: C, 61.01; H, 4.63; N, 3.39. Found: C, 59.94; H, 4.47; N, 3.26.

EXAMPLE 23

Benzyl 3-(p-nitrobenzenesulfonyloxy)-1-azabicyclo[3.2.0]hept-2-en-7-one-2-carboxylate

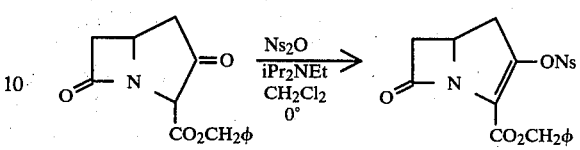

An ice-cold solution of benzyl 1-azabicyclo[3.2.0-]heptan-3,7-dione-2-carboxylate (20 mg, 0.077 mmol) in methylene chloride (2 ml) is treated with p-nitrobenzenesulfonic anhydride (37.3 mg, 0.096 mmol) and N,N-diisopropylethylamine (18.3 $\mu$l, 0.015 mmol). After stirring in the cold for 20 minutes, the solution is diluted with cold methylene chloride (1 ml) and cold 0.1 M pH 7 phosphate buffer (2 ml) and shaken. The organic phase is separated, washed with cold 0.1 M pH7 phosphate buffer (2×2 ml), water and brine, dried with magnesium sulfate, and filtered. The filtrate is diluted with cold methanol (0.5 ml) and quickly evaporated under vacuum to give a solid. The crude product is triturated with cold methanol and dried under vacuum to provide benzyl 3-(p-nitrobenzenesulfonyloxy)-1-azabicyclo[3.2.0]hept-2-en-7-one-2-carboxylate (26 mg) as a white solid: mp 86°–88°; IR (CH$_2$Cl$_2$) 1794, 1723, 1521, and 1344 cm$^{-1}$; UV (CHCl$_3$) 257 ($\epsilon$ 10,600) and 280 ($\epsilon$ 7,600) nm; NMR (CDCl$_3$) δ3.08 (dd, 1, J=3.6 and 17, H6$\beta$), 3.25 (dd, 1, J=8.8 and 18, H3a), 3.35 (dd, 1, J=9.8 and 18, H4b), 3.59 (dd, 1, J=5.4 and 17, H6$\alpha$), 4.26(m,1,H5), 5.10 (ABq, 2, J=21.2, CH$_2\phi$), 7.32 (s, 5, C$_6$H$_5$), 8.03 and 8.22 (two d's, 4, J=9.3, NO$_2$C$_6$H$_4$).

Preparation of p-nitrobenzene Sulfonic Anhydride

A mixture of p-nitrobenzenesulfonic acid (20 g), phosphorous pentoxide (50 g) and 1,2-dichloroethylene (100 ml) is heated at reflux for 4 days. The hot supernatant is decanted from the gummy residue and allowed to cool to room temperature. The resulting crystalline precipitate of p-nitrobenzenesulfonic anhydride (1.5 g) is collected, washed with anhydrous diethylether, and dried under vacuum. The gummy residue is twice more refluxed overnight with 100 ml portions of dichloroethylene and worked up as above to provide additional p-nitrobenzenesulfonic anhydride (4.0 g): mp 171°–172°.

EXAMPLE 24

BENZYL 3-DIPHENYLPHOSPHORYL-1-AZABICYCLO[3.2.0]HEPT-2-EN-7-ONE-2-CARBOXYLATE

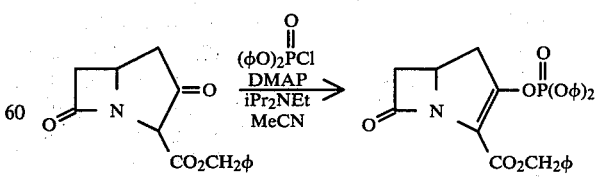

An ice-cold, stirring solution of benzyl 1-azabicyclo[3.2.0]heptan-3,7-dione-2-carboxylate (13 mg, 0.05 mMol), 4-dimethylamine pyridine (1.2 mg, 0.01 mMol) and N,N-diisopropylethylamine (12.2 $\mu$l, 0.07 mMol) in anhydrous acetonitrile (0.5 ml) is treated with diphenyl chlorophosphonate (12.4 μl, 0.06 mMol). The resulting solution is stirred in the cold and under a nitrogen atmosphere for 2 hours, then diluted with methylene chloride (5 ml), washed with water (2 ml), 0.1 M pH 7 phosphate buffer (2 ml) and brine, dried over magnesium sulfate, and filtered. Evaporation of the filtrate under vacuum leaves crude benzyl 3-diphenylphosphoryl-1-azabicyclo[3.2.0]-hept-2-en-7-one-2-carboxylate (22 mg) as an oil; UV (dioxane) 281 nm; NMR(CDCl$_3$) α 2.90 (dd,1,J=3 and 17, H6β), 3.17(m,2,H4a and H4b), 3.52 (dd,1,J=5.5 and 17, H6α), 4.13(m,1,H5), 5.28(S,2,CH$_2$φ), and 7.30(m,15,ArH).

EXAMPLE 25

N-(t-Butyldimethylsilyl)-4-[3-(p-nitrobenzyloxycarbonyl)-2-hydroxypropyl]-azetidin-2-one

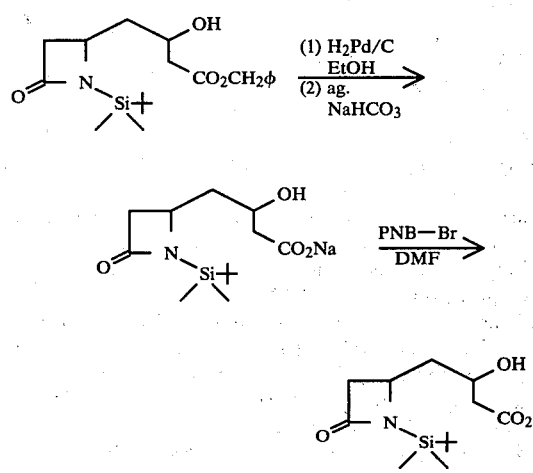

A mixture of crude N-(t-butyldimethylsilyl)-4-(3-benzyloxycarbonyl-2-hydroxypropyl)-azetidin-2-one (11.33 g, 30 mmol), ethanol (300 ml) and 10% palladium on charcoal (1.13 g) is hydrogenated at 50 psi for 1 hour. The mixture is filtered and the filtrate is treated with water (150 ml) containing sodium bicarbonate (2.52 g, 30 mmol) and concentrated under vacuum to ca 100 ml. The aqueous concentrate is washed with ethyl acetate (2×100 ml) and lyophilized to provide the sodium carboxylate (7.70 g) as a white powder.

The sodium salt and p-nitrobenzyl bromide (6.48 g, 30 mmol) are dissolved in anhydrous dimethyl formamide (150 ml) under a nitrogen atmosphere. After standing for 1 hour at room temperature, the solution is evaporated under vacuum to a semi-solid. The residue is taken up in ethyl acetate (200 ml), washed with water (2×200 ml) and brine, dried over magnesium sulfate, filtered, and evaporated under vacuum. The residual yellow oil is chromatographed on silica gel (250 g) using 1:1 toluene-ethyl acetate as eluting solvent to provide N-(t-butyldimethylsilyl)-4-[3-(p-nitrobenzyloxycarbonyl)-2-hydroxypropyl]-azetidin-2-one (8.92 g, 70%) as an oil which solidified on standing: IR (CH$_2$Cl$_2$) 3585, 1733, 1527, and 1350 cm$^{-1}$; NMR(CDCl$_3$) δ 0.22 (s,3,CH$_3$), 0.25 (s,3,CH$_3$), 0.93 (s,9,C(CH$_3$)$_3$), 1.16–2.33 (m,2,CH-CH$_2$-CH), 2.40–3.47 (m,3,OH and H3 and H3β), 2.55 (d,2,J=6, CH$_2$CO$_2$), 3.50–4.33 (m,2,H4 and CH—OH), 5.30 (s,2,CH$_2$Ar), and 7.55, 8.27 (two d's,4,J=8.5, ArH).

EXAMPLE 26

N-(t-Butyldimethylsilyl)-4-[3-(p-nitrobenzyloxycarbonyl)-2-hydroxypropyl]-azetidin-2-one

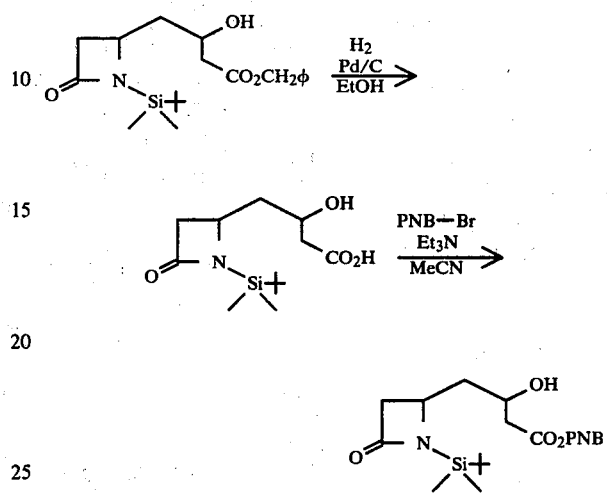

A mixture of crude N-(t-butyldimethylsilyl)-4-(3-benzyloxycarbonyl-2-Hydroxypropyl)-azetidin-2-one (13.46 g, 35.6 mmol), 10% palladium on charcoa, and ethanol (200 ml) is hydrogenated at 40 psi for 30 mins. The mixture is filtered and the filtrate is evaporated under vacuum and stripped with toluene to give N-(t-butyldimethylsilyl)-4-(3-carboxy-2-hydroxypropyl)-azetidin-2-one (9.51 g) as an off-white solid: IR (neat film from Me$_2$CO) 3200 (br), 1735, and 1700 (shifts to 1590 with Et$_3$N) cm$^{-1}$; NMR (Me$_2$CO-d$_6$) δ 0.25 (s,6,2CH$_3$), 0.98 (s,9,C(CH$_3$)$_3$) 1.17–2.33 (m,2,CH—C CH$_2$—CH), 2.50 (d,2,J=6.5, CH$_2$CO$_2$), 2.50–3.40 (m,2,H3 and H3β), 3.97 (m,2,H4 and CHOH); MS on bistrimethylsilyl derivative m/e 431 (M+), 416(M+ −57) and 332 (374−42).

The crude carboxylic acid is suspended in anhydrous acetonitrile (150 ml) and treated with p-nitrobenzyl bromide (7.56 g, 35 mμol) and triethylamine (4.9 ml, 35 mμol). The resulting solution is kept at room temperature for 2 days and then in a refrigerator for 3 days. The reddish orange solution is evaporated under vacuum and the residue shaken with ethyl acetate (100 ml, 2×50 ml) and filtered to remove triethylammonium bromide. The ethyl acetate filtrate is washed with water (3×100 ml) and brine, dried with magnesium sulfate, filtered, and evaporated under vacuum to an amber oil (13.62 g). Crystallization from diethyl ether affords N-(t-butyldimethylsilyl)-4-[3-(p-nitrobenzyloxycarbonyl)-2-hydroxypropyl]azetidin-2-one (6.84 g) as an off-white powder. Chromatography of the mother liquors on a silica gel column using 1:1 toluene-ethyl acetate as eluting solvent affords addition product (3.14 g) as an oil which solidifies.

EXAMPLE 27

N-(t-Butyldimethylsilyl)-4-[3-(p-nitrobenzyloxycarbonyl)-2-oxopropyl]-azetidine-2-one

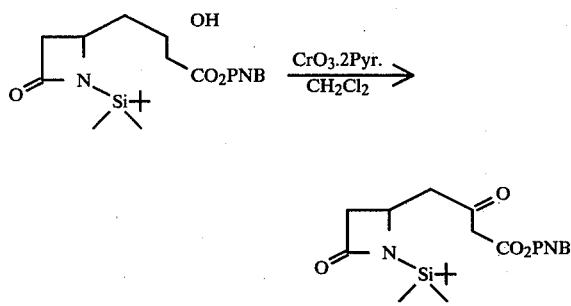

Anhydrous chromium trioxide (16.88 g 169 mmol) is added to a solution of anhydrous pyridine (27.3 ml, 338 mmol) in anhydrous methylene chloride (470 ml). The resulting mixture is stirred at room temperature for 30 minutes and then treated with a solution of N-(t-butyldimethylsilyl)-4-[3-(p-nitrobenzyloxycarbonyl)-2-hydroxypropyl]-azetidin-2-o one (8.92 g, 21.1 mmol) in methylene chloride (80 ml). The reaction mixture is stirred an additional 15 minutes at room temperature and then treated with 2-propanol (6.75 ml). The methylene chloride phase is decanted from the dark, tary residue and evaporated under vacuum. The residue from this operation is triturated with diethyl ether (350 ml) and filtered through a pad of magnesium sulfate which is washed with additional ether (150 ml). The ethereal filtrate is washed with water (200 ml), 5% aqueous sodium bicarbonate (200 ml) and brine, dried with magnesium sulfate, filtered, evaporated under vacuum, and stripped with toluene to afford the crude product (5.99 g) as an amber oil. Chromatigraphy on a silica gel column using 3:2 petroleum ether-ethyl acetate as eluting solvent yields N-(t-butyldimethylsilyl)-4-[3-(p-nitrobenzyloxycarbonyl)-2-oxopropyl]-azetidin-2-one (5.17 g, 58%) as a pale yellow, viscous oil which solidifies. Trituration with diethyl ether gives the product as small, white crystals: mp 65°–66.5°, IR (CH$_2$CL$_2$) 1732, 1522, and 1350 cm) NMR (CDCl$_3$) 8 0.20 (s,3,CH$_3$), 0.23 (s,3,CH$_3$), 0.93 (s,9,C(C$\underline{H}$$_3$)$_3$), 2.58 (dd,1,J=2.7 and 15.7, H3$\beta$), 2.72 (dd,1,J=9.4 and 18.2, C$\underline{H}$$_2$COCH$_2$CO$_2$), 3.19 (dd,1,J=4.0 and 18.2, C$\underline{H}$$_2$COCH$_2$CO$_2$), 3.35 (dd,1,J=5.3 and 15.7,H3$\alpha$), 3.55 (s,2,COCH$_2$CO$_2$), 3.90 (m,1,H4), 5.30 (s,2,CH$_2$Ar), 7.55 and 8.25 (two d$^{15}$,4,J-8.5, ArH); MS m/e 405 (M$^+$ −15), 363 (M$^+$ −57), 321 (363−42) and 136.

Anal, Calculated for C$_{20}$H$_{28}$N$_2$O$_6$Si: C,57.12; H,6.71; N,6.66. Found: C,57.28; H,6.75; N,6.60.

EXAMPLE 28

4-[3-(p-NITROBENZYLOXYCARBOYL)-2-OXOPROPYL]AZETIDIN-2-ONE

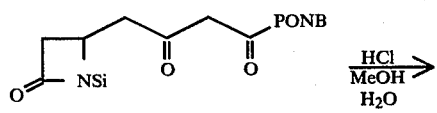

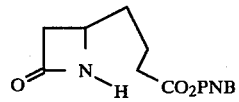

A solution of N-(t-butyldimethylsilyl)-4-[3-(p-nitrobenzyloxycarbonyl)-2-oxopropyl)]-azetidin-2-one (5.17 g, 12.3 mMol) in methanol (55 ml) is treated with 1 N hydrochloric acid (6.2 ml) and then kept at room temperature for 200 mins. The solution is treated with 1 M dipotassium hydrogenphosphate (6.2 ml) and concentrated under vacuum. The residue is taken up in ethyl acetate (100 ml), washed with brine, dried over magnesium sulfate, filtered, and evaporated under vacuum. Triturating the resulting oil with diethyl ether yields 4-[3-(p-nitrobenzyloxycarbonyl)-2-oxopropyl]-azetidin-2-one (3.42 g, 91%) as an off-white powder: mp 50°–52°; IR (CH$_2$Cl$_2$) 3416, 1767, 1723, 1528, and 1352 cm$^{-1}$; NMR (CDCl$_3$) $\alpha$2.60 (ddd,I,J=1,2.7, and 15.1,H3$\beta$), 2.77 (dd,1,J=8.4 and 18.2, CHC$\underline{H}$$_2$CO), 3.13 (dd,1,J=5.1 and 18.2, CHC$\underline{H}$$_2$CO), 3.20 (ddd,I,J=2.4, 5.0, and 15.1, H3$\alpha$), 3.57 (s,2,COCH$_2$CO$_2$), 3.98 (m,1,H4); 5.27 (s,2,CH$_2$Ar), 6.28 (br s,1,NH), 7.53 and 8.23 (two d's,4,J=8.5, ArH); mass spectrum m/e 306(M+), 264(M+ −42), 237, 153, 125, 111, and 136.

EXAMPLE 29

4-[3-p-NITROBENZYLORYCARBONYL)-3-DIAZO-2-OXOPROPYL]AZETIDIN-2-ONE

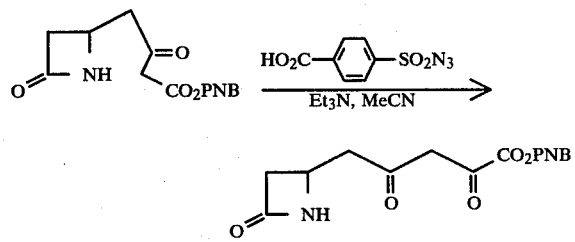

p-Carboxybenzyenesulfonylazide (2.67 g, 11.8 mMol) and triethylamine (4.68 ml, 33.6 mMol) are added to an ice-cold, stirring solution of 4-[3-(p-nitrobenzyloxycarbonyl)-2-oxopropyl]-azetidin-2-one (3.42 g, 11.2 mMol) in anhydrous acetonitrile (70 ml). The resulting mixture is stirred in the cold for 10 minutes and at room temperature for 60 minutes. The mixture is diluted with ethyl acetate (200 ml) and filtered. The filtrate is washed with water (2×100 ml), 1 M pH3 phosphate buffer (50 ml), 0.1 M pH7 phosphate buffer (100 ml), and brine, dried over magnesium sulfate, filtered, and evaporated under vacuum to a yellow foam (3.75 g). The crude product is taken up in methylene chloride (ca. 10 ml), heated briefly with activated charcoal, and filtered through a pad of magnesium sulfate. The filtrate is diluted with diethyl ether (ca. 40 ml) and scratched to yield a precipitate. The precipitate is collected, washed with ether, and dried under vacuum to provide 4-[3-(p-nitrobenzyloxycarbonyl)-3-diazo-2-oxopropyl]-azetidin-2-one (3.29 g, 88%) as a pale yellow powder: mp 114.5°–116.5°; IR (CH$_2$Cl$_2$) 3413, 2142, 1767, 1724, 1657, 1530, and 1352 cm$^{-1}$; NMR (CDCl$_3$) $\alpha$2.68 (ddd,1, J=1.2, 2.7, and 14.8, H3$\beta$), 3.02 (dd,1,J=8.4 and 18.0, CHC$\underline{H}$$_2$CO), 3.22 (ddd,1,J=2.4, 4.8, and 14.8, H3$\alpha$); 343 (dd,1,J=4.6 and 18.0, CHC$\underline{H}$$_2$CO), 4.00 (m,1, H4), 5.38 (s,2,CH₂Ar), 6.30 (brs,1,NH), 7.57 and 8.27 (two d's,4,J=8.5, ArH); mass spectrum m/e 332(M+), 304(M+ −28), 290(M+ −42), 262, and 263.

Anal., calculated for $C_{14}H_{12}N_4O_6$: C,50.61; H,3.64; N,16.86.

Found: C,50.34; H,3.42; N,16.72.

EXAMPLE 30

P-NITROBENZYL 1-AZABICYCLO[3.2.0]HEPTAN-3,7-DIONE-2-CARBOXYLATE

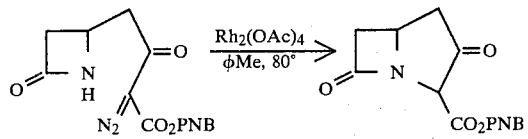

A suspension of 4-[3-(p-nitrobenzylocycarbonyl)-3-diazo-2-oxopropyl]-azetidin-2-one (2.93 g) and rhodium (II) acetate (15 mg) in anhydrous toluene (300 ml) is degassed by bubbling nitrogen through it for 60 minutes. The mixture is then stirred and heated in an oil bath maintained at 80° C. After a few minutes, the diazo compound dissolves and gas evolution commences. The mixture is heated at 80° C. for 100 minutes, then allowed to stand at room temperature for 30 mins. before filtering through a pad of celite. The filtrate is evaporated under vacuum to an oily residue which is triturated with diethyl ether to afford p-nitrobenzyl 1-azabicyclo[3.2.0]heptan-3,7-dione-2-carboxylate (2.53 g, 94%) as an off-white powder. Recrystallization from ether provides analytically pure product: mp 127°-128°: IR ($CH_2Cl_2$) 1776, 1753, 1529, and 1352 cm⁻¹; NMR (CDCl₃) α 2.47 (dd,1,J=8.2 and 18.8, H4a), 2.98 (dd,1,J=6.8 and 18.8, H4b), 3.00 (dd,1, J=2.0 and 12.0, H6β), 3.70 (dd,1,J=4.8 and 12.0, H6α), 4.20 (m,1, H5), 4.80 (s,1,H2), 5.32 (s,2,CH₂Ar), 7.57 and 8.25 (two d's,4,J=8, ArH); mass spectrum m/e 304(M+), 276(M+ −28), 262 (M+ −42), and 168(M+ −136).

Anal., calculated for $C_{14}H_{12}N_2O_6$: C,55.27; H,3.98; N,9.21.

Found: C,55.06; H,4.03; N,8.99.

EXAMPLE 31 p-Nitrobenzyl 3-(p-Toluenesulfonyloxy)-1-azabicyclo [3.2.0]hept-2-en-7-one-2-carboxylate

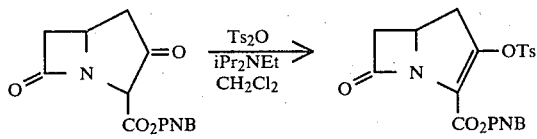

p-toluenesulfonic anhydride (520 mg, 1.59 m·μol) and N,N-diisopropylethylamine (300 μl, 1.72 m·μol) are added to an ice-cold, stirring solution of p-nitrobenzyl 1-azabicyclo[3.2.0]heptan-3,7-dione-2-carboxylate (484 mg, 1.59 m·μol) in anhydrous methylene chloride (17 ml). The resulting solution is stirred in the cold for 2 hours, then diluted with more methylene chloride, washed with water, 1μ ph 3.4 phosphate buffer and saturated aqueous sodium bicarbonate, dried with magnesium sulfate, filtered, and evaporated under vacuum. Addition of cold ethyl acetate and a few seed crystals to the oily residue induces crystallization. The product is collected, washed with cold ethyl acetate, and dried under vacuum to afford p-nitrobenzyl 3-(p-toluenesulfonyloxy)-1-azabicyclo [3.200]hept-2-en-7-one-2-carboxylate (446 mg, 61%) as off-white crystals: mp 99°-102° (dec.); IR (neat) 1790, 1725, 1521, 1345, and 1172 cm⁻¹; UV ($CH_2Cl_2$) 272 nm; NMR (CDCl₃) δ 2.40 (s,3,ArCH₃), 3.06 (dd,1,J=3.0 and 17.2, HGβ), 3.16 (dd,1,J=9.0 and 9.0,H4a), 3.31 (dd,1,J=9.0 and 10.0, H46), 3.59 (dd,1,J=5.8 and 17.2, HG), 4.24 (m,1,H5), 5.20 and 5.32 (ABq,2,J=14.0,CH₂Ar), 7.32 and 7.77 (two d's,4,J=8.0, p-MeC₆H₄), 7.51 and 8.19 (two d's,4,J=8.0,p-NO₂C₆H₄).

EXAMPLE 32

Benzyl 3-methoxy-1-azabicyclo[3.2.0]hept-2-en-7-one-2-carboxylate

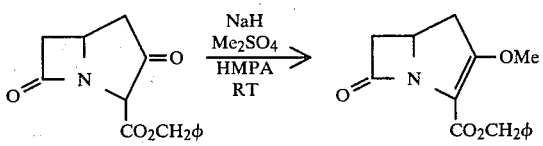

A solution of benzyl 1-azabicyclo[3.2.0]heptan-3,7-dione-2-carboxylate (25.9 mg, 0.1 mMol) in anhydrous hexamethylphosphoramide (1.0 ml) is cooled in an ice-bath and stirred under a nitrogen atmosphere. Dimethyl sulfate (11.4 μl, 0.12 mMol) and 57% sodium hydride in mineral oil (5.0 mg, 0.12 mMol) are added to the solution. The cooling bath is removed and the resulting mixture is stirred at room temperature for 60 minutes. The mixture is diluted with ethyl acetate (10 ml) and water (20 ml), shaken, and the layers separated. The organic layer is washed with water (3×5 ml) and brine, dried with magnesium sulfate, diluted with toluene (10 ml), and evaporated under vacuum to an oil. This material is chromatographed on a 0.25 mm×10×20 cm silica gel GF plate using 3:1 toluene-ethyl acetate as developing solvent. The major UV visible band at R_f 0.1 was removed and eluted with ethyl acetate to provide benzyl 3-methoxy-1-azabicyclo[3.2.0]hept-2-en-7-one-2-carboxylate (5.6 mg) as a clear oil: IR ($CH_2Cl_2$) 1775 and 1700 cm⁻¹; UV (EtOAc) 288 nm; NMR (CDCl₃) δ2.87 (dd, 1, J=2.8 and 16, H6β), 3.03 (m, 2, H4a and H4b), 3.50 (dd, 1, J=5.5 and 16, H6α), 3.80 (m, 1, H5), 3.92 (s, 3, CH₃), 5.28 (s, 2, CH₂φ), and 7.40 (m, 5, C₆H₅); mass spectrum m/e 273 (M+) and 231 (M+ −42).

This product is also obtained by treating the bicyclo keto ester with dimethyl sulfate and excess potassium carbonate in hexamethylphosphoramide or dimethylformamide.

EXAMPLE 33

Following the foregoing examples and text there are prepared the following compounds in an analogous manner:

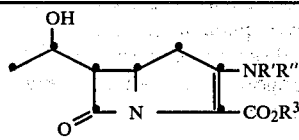

| Compound | R' | R" | R³' |
|---|---|---|---|
| (1.) | —CH₃ | H | Na |
| (2.) | i-propyl | H | Na |
| (3.) |  | H | Na |
| (4.) | CH₂CH₂CH(CH₃)₂ | H | Na |
| (5.) | CH₂CH₂OH | H | Na |
| (6.) | CH₂CH₂CH₂OH | H | Na |
| (7.) | CH₂CH₂CH₂NH₂ | H | H |
| (8.) | CH₂CH₂N(morpholino) | H | H |
| (9.) | CH₂CH₂N(pyrrolidino) | H | H |
| (10.) | CH₂—C₆H₄—Cl | H | Na |
| (11.) | CH₂—pyridyl | H | H |
| (12.) | CH₃ | CH₃ | Na |
| (13.) | CH₂CH₃ | CH₂CH₃ | Na |
| (14.) | CH₃CH₂CH₂ | CH₃ | Na |
| (15.) | CH₂CH₂N(CH₃)₂ | CH₃ | H |
| (16.) | CH₂CH₂φ | CH₃ | Na |
| (17.) | —(CH₂)₅— | | Na |
| (18.) | —CH₂CH₂—O—CH₂CH₂— | | Na |
| (19.) | —CH₂CH₂N(CH₃)CH₂CH₂— | | H |

EXAMPLE 34

Preparation of Pharmaceutical Compositions

One such unit dosage form comprises 120 mg of 6-(1-hydroxyethyl)-3-[N-methyl-N-(2-dimethylaminoethyl)amino]-1-azabicyclo[3.2.0]hept-2-en-7-one-2-carboxylic acid with 20 mg of lactose and 5 mg of magnesium stearate and placing the 145 mg mixture into a No. 3 gelatin capsule. Similarly, by employing more of the active ingredient and less lactose, other dosage forms can be put up in No. 3 gelatin capsules and shoult it be necessary to mix more than 145 mg of ingredients together, larger capsules such as compressed tablets and pills can also be prepared. The following examples are illustrative of the preparation of pharmaceutical formulations:

| TABLET | PER TABLET |
|---|---|
| 6-(1-hydroxyethyl)-3-[N—methyl-N—(2-dimethylaminoethyl)amino]-1-azabicyclo [3.2.0] hept-2-en-7-one-2-carboxylic acid | 125 mg. |
| Cornstarch, U.S.P. | 6 mg. |
| Dicalcium Phosphate | 192 mg. |
| Lactose, U.S.P. | 190 mg. |

The active ingredient is blended with the dicalcium phosphate, lactose and about half of the cornstarch. The mixture is then granulated with 15% cornstarch paste (6 mg) and rough-screened. It is dried at 45° C. and screened again through No. 16 screens. The balance of the cornstarch and the magnesium stearate is added and the mixture is compressed into tablets, approximately 0.5 inch in diameter each weighing 800 mg.

| PARENTERAL SOLUTION | |
|---|---|
| Ampoule: | |
| 6-(1-hydroxyethyl)-3-[N—methyl-N—(2-dimethylaminoethyl)amino]-1-azabicyclo[3.2.0] hept-2-en-7-one-2-carboxylic acid | 500 mg. |
| OPTHALMIC SOLUTION | |
| 6-(1-hydroxyethyl)-3-[N—methyl-N—(2-dimethylaminoethyl)amino]-1-azabicyclo[3.2.0] hept-2-en-7-one-2-carboxylic acid | 100 mg. |
| Hydroxypropylmethyl | 5 mg. |
| Sterile Water to | 1 ml. |
| OTIC SOLUTION | |
| 6-(1-hydroxyethyl)-3-[N—methyl-N—(2-dimethylaminoethyl)amino]-1-azabicyclo[3.2.0] hept-2-en-7-one-2-carboxylic acid | 100 mg. |
| Benzalkonium chloride | 0.1 mg. |
| Sterile Water to | 1 ml. |
| TOPICAL OINTMENT | |
| 6-(1-hydroxyethyl)-3-[N—methyl-N—(2-dimethylaminoethyl)amino]-1-azabicyclo[3.2.0] hept-2-en-7-one 2-carboxylic acid | 100 mg. |
| Polyethylene Glycol 4000 U.S.P. | 400 mg. |
| Polyethylene Glycol 400 U.S.P. | 1.0 gram |

The active ingredient in the above formulations may be administered alone or in combination with other biologically active ingredients, as for example, with other antibacterial agents such as lincomycin, a penicillin, streptomycin, nonobiocin, genatmicin, neomycin, colistin and kanamycin, or with other therapeutic agents such as probenecid.

What is claimed is:

1. A compound having the structural formula:

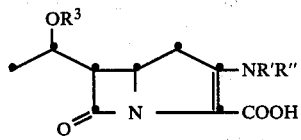

and the pharmaceutically acceptable salts thereof; wherein: R³ is H, or is selected from the group consisting of: formyl, acetyl, propionyl, butyryl, chloroacetyl, methoxyacetyl, aminoacetyl, methoxycarbonyl, ethoxycarbonyl, methylcarbamoyl, ethylcarbamoyl, phenylthiocarbonyl, 3-aminopropionyl, 4-aminobutyryl, N-methylaminoacetyl, N,N-dimethylaminoacetyl, 3-(N,N-dimethyl)amino propionyl, guanidinoacetyl, 3-guanidinopropionyl, $N^3$-methylguanidinopionyl, hydroxyacetyl, 3-hydroxypropionyl, acryloyl, propynoyl, malonyl, phenoxycarbonyl, amidinoacetyl, acetamidinoacetyl, amidinopropionyl, acetamidinopropionyl, guanylureidoacetyl, guanylcarbamoyl, carboxymethylaminoacetyl, sulfoacetylaminoacetyl, phosphonoacetylaminoacetyl, $N^3$-dimethylaminoacetamidinopropionyl, uredocarbonyl, dimethylaminoguanylthioacetyl, 3(5-aminoimidazol-1-yl)-propionyl, 3-sydnonylacetyl, o-aminomethylbenzoyl, o-aminobenzoyl, sulfo, phosphono,

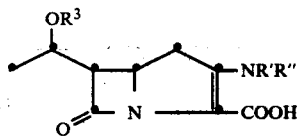

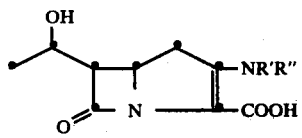

and R' and R" are independently selected from the group consisting of hydrogen, substituted with 1-3 substituents and unsubstituted: alkyl and cycloalkyl having 1-10 carbon atoms, phenylalkyl and heterocyclyalkyl wherein the alkyl moiety was 1-6 carbon atoms and the heterocyclyl is selected from the group consisting of:

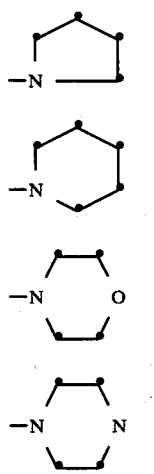

and the cyclic group formed by the joining of R' and R" is selected from:
—(CH$_2$)$_5$—
—CH$_2$CH$_2$—O—CH$_2$—CH$_2$—

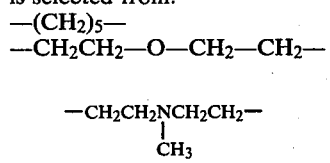

wherein the ring or chain substituent or substituents on R', R" or the cyclic radical formed by their joinder are selected from: amino, mono- and dialkylamino (each alkyl having 1-6 carbon atoms), hydroxyl, carboxyl, alkoxyl having 1-6 carbon atoms chloro, bromo, fluoro, nitro, sulfamoyl, phenyl, benzyl, and alkoxylcarbonyl having 1-3 carbon atoms in the alkoxyl moiety.

2. A compound according to claim 1 having the structural formula:

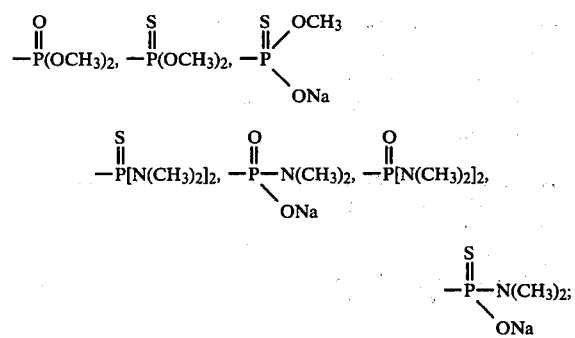

wherein R$^3$ is hydrogen.

3. A compound having the structural formula:

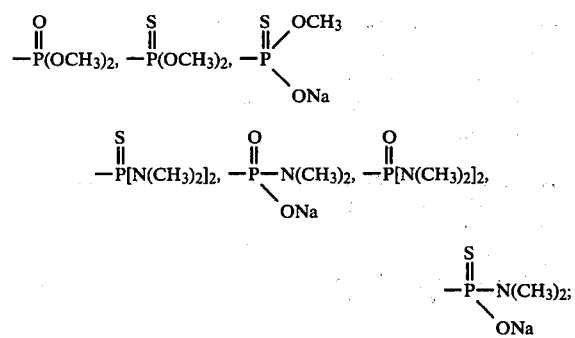

and the pharmaceutically acceptable salts thereof; wherein: the 3-substituent —NR'R" is selected from the group consisting of:
—NH$_2$,
—NHCH$_2$CH$_3$,
—NH(CH$_2$)$_2$CH$_3$,
—NHCH(CH$_3$)$_2$,
—NHCH(CH$_3$)CH$_2$CH$_3$,
—NHCH$_2$CH(CH$_3$)$_2$,
—NH(CH$_2$)$_2$CH(CH$_3$)$_2$,
—NH(CH$_2$)$_2$C(CH$_3$)$_3$,
—NHCH(CH$_3$)(CH$_2$)$_4$CH$_3$,
—NHCH(CH$_3$)CH(CH$_3$)$_2$,

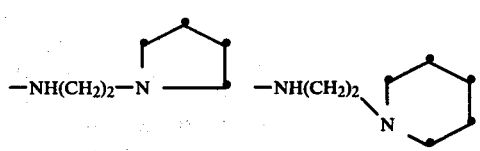

—NHCH$_2$CH$_2$OH,
—NHCH(CH$_2$CH$_3$)CH$_2$OH,
—NH(CH$_2$)$_4$CH$_2$OH,
—NHCH(CH$_3$)CH$_2$OH,
—NHCH$_2$C(CH$_3$)$_2$OH,
—NH(CH$_2$)$_2$CH$_2$OH,
—NH(CH$_2$)$_3$CO$_2$CH$_2$CH$_3$,
—NH(CH)CH$_3$CH$_2$CO$_2$CH$_2$CH$_3$,
—NHCH$_2$CH$_2$OCH$_3$,
—NHCH$_2$CF$_3$,
—NHCH$_2$CH$_2$N(CH$_3$)$_2$,
—NH(CH$_2$)$_3$N(CH$_3$)$_2$,
—NHCH(CH$_3$)(CH$_2$)$_3$N(C$_2$H$_5$)$_2$,

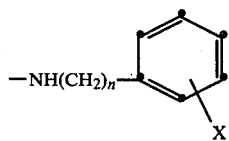

(n=1-3; X=H, CH₃, OCH₃, Cl, Br, F, NO₂, OH, SO₂NH₂),

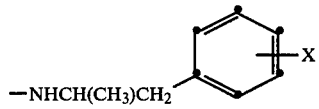

(X=OH, CH₃),
—NHCH₂CH(φ)₂ (φ=phenyl),
—NHCH₂CH(φ)CH₂OH

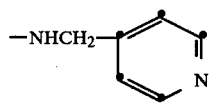

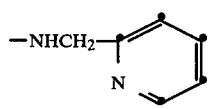

—NHCH₃,
—N(C₂H₅)₂,
—N(CH₂CH₂CH₃)₂,
—N(CH₂CH₂CH₂CH₃)₂,

—N(CH₃) (CH₂CH₃),
—N(CH₂CH₃)CH₂CH₂N(C₂H₅)₂,
—N(CH₃) (CH₂CH₂CH₂CH₃),

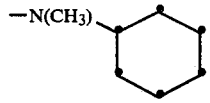

—N(CH₂CH₂OCH₂CH₃)₂,
—N(CH₂CH₂CH₂CH₃)CH₂CH₂OH,
—N(CH₃)CH₂CH₂N(CH₃)₂,
—N(CH₂CH₃) (CH₂CH₂CH₂CH₃),
—N(CH₂CH₃) (CH₂CH₂OH),
—N(CH₂CH₂OH)₂,
—N(CH₃)CH₂φ
—N(CH₂φ)CH₂CH₂N(CH₃)₂,
—N(CH₂φ)CH₂CH₂OH,
—N(CH₃)CH₂CH(OH)φ,
—N(CH₂CH₃)CH₂φ,

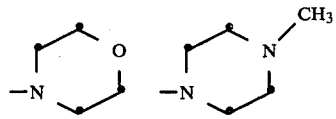

4. An antibacterial pharmaceutical composition comprising, in unitary dosage form, a therapeutically effective amount of a compound according to claim 1 and a pharmaceutical carrier therefor.

* * * * *